United States Patent [19]

Gylys et al.

[11] Patent Number: 5,521,188

[45] Date of Patent: May 28, 1996

[54] ANTIMIGRAINE CYCLOBUTENEDIONE DERIVATIVES OF INDOLYLALKYL-PYRIDINYL AND PYRIMIDINYLPIPERAZINES

[75] Inventors: Jonas A. Gylys, Southington, Conn.; Edward H. Ruediger, Quebec, Canada; David W. Smith, Madison, Conn.; Carola Solomon, Quebec, Canada; Joseph P. Yevich, Southington, Conn.; Pierre Dextraze, Quebec, Canada

[73] Assignee: Bristol-Myers Squibb Company, Princeton, N.J.

[21] Appl. No.: 277,789

[22] Filed: Jul. 25, 1994

Related U.S. Application Data

[63] Continuation-in-part of Ser. No. 122,266, Sep. 16, 1993, abandoned.

[51] Int. Cl.$^6$ ............. A61K 31/495; A61K 31/505; C07D 401/14; C07D 403/14
[52] U.S. Cl. ............. 514/253; 544/295; 544/364
[58] Field of Search ................. 544/333, 364, 544/295; 514/253

[56] References Cited

U.S. PATENT DOCUMENTS

| | | | |
|---|---|---|---|
| 5,077,293 | 12/1991 | Smith et al. | 514/253 |
| 5,300,506 | 4/1994 | Smith et al. | 514/253 |
| 5,434,154 | 7/1995 | Smith et al. | 514/239 |

FOREIGN PATENT DOCUMENTS

| | | |
|---|---|---|
| 0426379 | 5/1991 | European Pat. Off. . |
| 0464558 | 1/1992 | European Pat. Off. . |
| 0548813 | 6/1993 | European Pat. Off. . |
| 1551082 | 12/1968 | France . |
| WO94/01436 | 1/1994 | WIPO . |

OTHER PUBLICATIONS

Edmeads, *J. Internal Medicine*, ed. by Stein, J. H. et al. (Mosby, St. Louis), pp. 1029, 1032 (1994).

*Primary Examiner*—Mukund J. Shah
*Assistant Examiner*—King L. Wong
*Attorney, Agent, or Firm*—Richard P. Ryan

[57] ABSTRACT

A series of novel 5-cyclobutenedione derivatives of indolylalkylpiperazinyl pyridines and pyrimidines of Formula I are intended for use in the alleviation of vascular headaches.

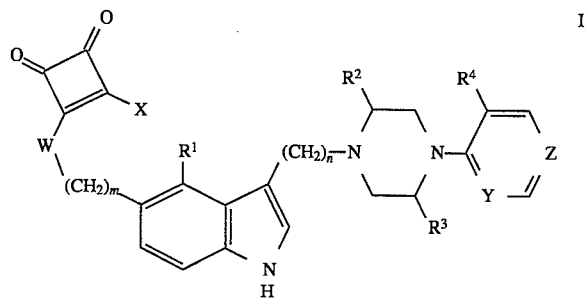

10 Claims, No Drawings

ANTIMIGRAINE CYCLOBUTENEDIONE DERIVATIVES OF INDOLYLALKYL-PYRIDINYL AND PYRIMIDINYLPIPERAZINES

CROSS REFERENCE TO RELATED APPLICATION

This application is a continuation-in-part of our application, Ser. No. 08/122,266 filed Sep. 16, 1993, now abandoned.

BACKGROUND OF THE INVENTION

This invention generally pertains to heterocyclic carbon compounds having drug and bio-affecting properties and to their preparation and use. In particular the invention is concerned with 1,4-disubstituted piperazine derivatives wherein one substituent moiety is a cyclobutenedione-substituted indol-3-yl-alkyl group and the other moiety is a pyridinyl or pyrimidinyl ring. These compounds possess a unique serotonergic profile that renders them useful in treatment of vascular headaches such as migraine or cluster type.

Archer disclosed a large series of CNS-depressant indolylalkylpiperazines in U.S. Pat. No. 3,188,313. Among a large number of possible substituents on the 4-nitrogen atom of the piperazine ring was pyrimidine. In U.S. Pat. No. 3,562,278, Archer disclosed and claimed a series of 1-indolylethyl-4-substituted-piperazines. Among the possible 4-substituents listed is 2-pyrimidinyl. The pharmacologic action disclosed for these art compounds is general CNS and psychomotor depression which bear no relationship to an antimigraine therapeutic agent.

Dowie, et al. disclosed a series of 3-alkylaminoindole derivatives as being potentially useful for the treatment of migraine in a published patent application, GB 2,124,210. One member of this series of compounds was specifically claimed in a later patent application of Oxford, GB 2,162,522, published Feb. 5, 1986. This particular compound is known in the literature as sumatriptan(i).

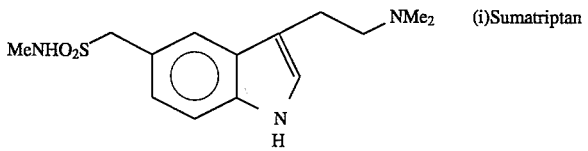

(i)Sumatriptan

A series of novel indoline derivatives were disclosed Feb. 7, 1990 by Manoury, et al., in European patent application EPA 354,094. These compounds are described as being useful for treatment of various CNS disorders including depression, anxiety and migraine. Included among these art compounds are those of formula (ii)

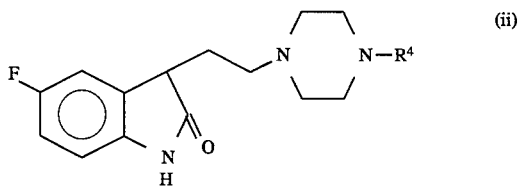

wherein $R^4$ is aryl, pyridine or quinoline moieties.

Smith, et al. in U.S. Pat No. 4,954,502 have disclosed a series of 1,4-disubstituted piperazine derivatives of formula (iii) which are useful as antidepressant agents.

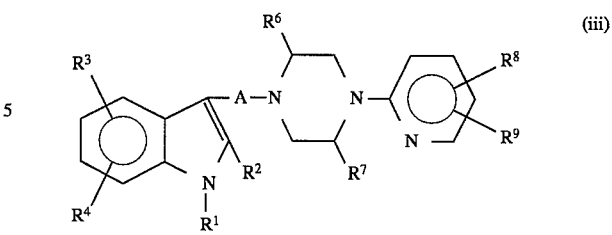

The indolyl substituents $R^3$ and $R^4$ were hydrogen, alkyl, alkoxy, alkylthio, halogen, carboxamide, and trifluoromethyl.

Another series of antidepressant 1,4-disubstituted piperazines where pyrimidine moieties were used instead of pyridine was set forth by Smith, et al. in U.S. Pat. No. 5,077,293.

The most relevant background is believed to be our earlier work which disclosed antimigraine alkoxypyrimidine derivatives of formula (iv)

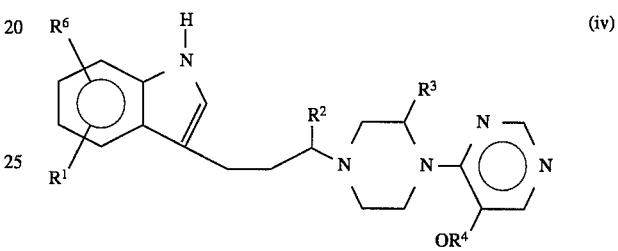

wherein the indole substituents ($R^1$ and $R^6$) were halogen, hydroxy, alkoxy and sulfonamido.

None of these art compounds suggest the instant novel 5-cyclobutenedione-substituted-indol-3-ylalkyl derivatives of pyridinyl or pyrimidinylpiperazines for the treatment of migraine and cluster-type headaches.

Migraine is a member of a broader class of headache that also comprises cluster headaches and other headaches believed to have a vascular implication in their etiology. These headaches are often classified as vascular headaches. For a current summary of headache and its treatment see: Chapter 13: "Drugs Used to Treat Migraine and Other Headaches" in *Drug Evaluations, 6th Edn.*, 1986, pages 239–253 American Medical Association, W. B. Saunders Co., Philadelphia, Pa.

Frequent irregularly-occurring episodes of headache afflict a large number of people but are usually acute in nature and of short duration. Relief of this type of headache is typically provided by mild analgesics such as aspirin or acetaminophen. Such headaches are quite common and, while painful and perhaps annoying, are seldom incapacitating and debilitating. Chronic recurrent headaches of the vascular category, however, usually lead to patient consultation with a physician due to pain severity which is often incapacitating.

Although there is no universally accepted classification system for headache, vascular headache, for the purposes of the present invention, refers mainly to migraine and cluster headaches. Migraine includes the common or classical type as well as migraine variants which would be familiar to one skilled in the art. Other subtypes such as toxic vascular and hypertensive headaches, chronic paroxysmal hemicrania, as well as some muscle-contraction and combined or mixed vascular-muscle headaches may also fall into a vascular-related headache category and be treatable by the present invention. It is appreciated by one skilled in the art that no single therapy is effective in all patients diagnosed with the same subtype of headache, thereby raising further uncertainties about headache classification.

Drugs most commonly used in treatment of headache fall into the following groups:

Ergot Alkaloids,
Beta-blocking Agents,
Calcium Channel Blocking Agents,
Antidepressants, and
Mixtures of these.

Management of recurring vascular headache is complicated by the lack of a single therapy which is effective in all patients with the same headache type and by the need to select either an abortive or prophylactic method of treatment for these headaches. Further complication involves the current use of drugs that cause dependence with extended use, such as ergotamine. Another important consideration for the present invention is that the more effective antimigraine agents in current use, e.g. the ergots, and methysergide, produce severe use-limiting side-effects with long term usage.

Thus there is a need for a safe and effective drug for the treatment of migraine and related disorders which can be used either prophylactically or to alleviate an established headache.

The objectives of the present invention relate to the use of novel cyclobutenedione-substituted-indol-3-ylalkyl derivatives of pyridinyl- and pyrimidinylpiperazines to provide treatment of vascular headaches, particularly migraine and cluster-types; to processes for their preparation; and to their pharmaceutical compositions and medical usage.

SUMMARY AND DETAILED DESCRIPTION OF THE INVENTION

The method of the present invention is intended for the alleviation of vascular or vascular-related headache of which migraine and cluster are the best known specific examples. The method essentially involves administration of a cyclobutenedionesubstituted indol-3-ylalkyl derivative of a pyridinyl or pyrimidinylpiperazine, or a pharmaceutically acceptable salt and/or solvate thereof, to a human in need of such treatment. For use in the instant method, oral and transnasal administration of pharmaceutical compositions containing the subject antimigraine agents are preferred.

In a broad aspect, the present invention is concerned with indol-3-ylalkyl derivatives of pyridinyl or pyrimidinylpiperazines having useful antimigraine serotonergic properties and characterized by Formula I.

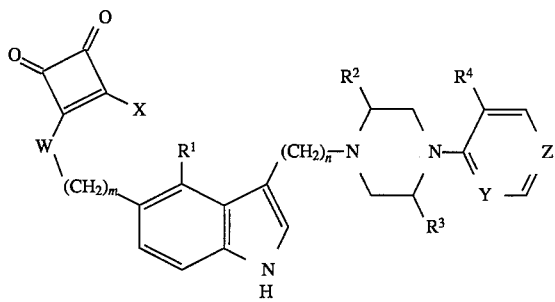

I

In Formula I, $R^1$ is a substituent selected from hydrogen, halogen, lower alkyl, lower alkoxy, and lower alkylthio.

$R^2$ and $R^3$ are independently selected from hydrogen and lower alkyl. In preferred compounds $R^2$ and $R^3$ are usually not lower alkyl at the same time.

$R^4$ can be hydrogen or lower alkoxy.

The integers 1 to 3 or zero can be selected for m while n can be the integers 1 to 5. In preferred compounds, m is zero and n is 3.

W can be either a single covalent carbon-carbon bond or $-NR^5-$, where $R^5$ is selected from hydrogen, lower alkyl, lower acyl, and lower alkylsulfonyl.

X is selected from $-NR^2R^3$; $-OR^2$; and $R^6$, with $R^6$ being hydrogen, lower alkyl, cycloalkyl, aryl, or aryl-lower alkyl.

Y and Z are independently selected from N and CH with the proviso that both Y and Z cannot be CH simultaneously.

Additionally, compounds of Formula I also encompass all pharmaceutically acceptable acid addition salts and/or solvates thereof. The present invention is also considered to include stereoisomers as well as optical isomers e.g. mixtures of enantiomers as well as individual enantiomers and diasteromers, which arise as a consequence of structural asymmetry in certain compounds of the instant series. Separation of the individual isomers is accomplished by application of various methods which are well known to practitioners in the art.

The term "lower alkyl" refers to both straight and branched chain carbon radicals of from 1 to 4 carbon atoms inclusive. Illustrative of these radicals are carbon chains which can be methyl, ethyl, propyl, isopropyl, 1-butyl, 1-methylpropyl, 2 methylpropyl. The term "lower acyl" denotes an acyl group containing from 1 to 4 carbons, e.g. a formyl group, a butyryl group, etc.

Lower alkoxy and lower alkylthio refer to $C_{1-4}$ alkyl groups connected to an oxygen or sulfur atom, respectively. Lower alkylsulfonyl refers to a $C_{1-4}$ alkyl group conected to a "$-SO_2-$" moiety.

"Cycloalkyl" refers in this instance to $C_{5-7}$ carbocyllic rings such as cyclopentyl, cyclohexyl or cycloheptyl groups. The term "aryl-lower alkyl" refers to phenalkyl groups having alkyl links of from 1 to 4 carbons. By appropriate selection of Y and Z either a pyridine or a pyrimidine ring is designated.

The pharmaceutically acceptable acid addition salts of the invention are those in which the counter-ion does not contribute significantly to the toxicity or pharmacological activity of the salt and, as such, they are the pharmacological equivalents of the bases of Formula I. They are generally preferred for medical usage. In some instances, they have physical properties which makes them more desirable for pharmaceutical formulation such as solubility, lack of hygroscopicity, compressibility with respect to tablet formation and compatibility with other ingredients with which the substance may be used for pharmaceutical purposes. The salts are routinely made by admixture of a Formula I base with the selected acid preferably by contact in solution employing an excess of commonly used inert solvents such as water, ether, benzene, methanol, ethanol, ethyl acetate and acetonitrile. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. Pharmaceutically acceptable acids for the purposes of salt formation of the substances of Formula I include sulfuric, phosphoric, hydrochloric, hydrobromic, hydroiodic, citric, acetic, benzoic, cinnamic, fumaric, mandelic, phosphoric, nitric, mucic, isethionic, palmitic, heptanoic, and others.

The compounds of Formula I can be prepared by adaptation of the synthetic processes shown in Schemes A and B. Processes for syntheses of some intermediate compounds are outlined in Scheme C. In addition, certain compounds and their syntheses will be set forth in more detail in the Specific Embodiments section, infra.

In the synthetic schemes, $R^1$ through $R^6$, W, X, Y, Z, m and n are as defined supra. The symbol Q represents a synthetic organic leaving group moiety such as tosyl, mesyl, halide, sulfate, phosphate, and so forth. Tosylate is also denoted Ts when it is the specified moiety. The symbol i—Pr denotes isopropyl and TIPS refers to the tri-isopropylsilyl group (—Si(i—Pr)$_3$).

Scheme A sets out the processes for synthesizing compounds of Formula I wherein W is —NR$^5$. The processes proceed either via the 5-amino-substituted intermediate of formula (6) wherein the heterocyclic- substituted-piperazine moiety is already incorporated into the molecular structure or via intermediate (20) wherein the indolyl-amino-squarate moiety is elaborated initially. Selection of synthetic paths depends on the nature of the desired X-substituent on the squarate moiety as well as the desired identity of the $R^5$ substituent.

Scheme B deals with synthetic pathways for compounds of Formula I wherein W is a covalent chemical bond. The choice of synthetic pathways proceeding from intermediate (11) depends on selection of substituent X that is desired. The Scheme B processes elaborate the squarate sub-structure prior to coupling the indolylalkyl moiety with the heterocyclic-substituted-piperazine.

Scheme C sets forth, by way of example, two typical syntheses which provide several starting intermediates for Schemes A and B.

The reactions employed in Schemes A–C and their application are familiar to the practitioner skilled in organic synthesis and modifications of conditions and reagents would be readily understood. The skilled synthetic chemist would know how to adapt these processes for preparation of specific Formula I compounds including other compounds embraced by this invention but not specifically disclosed. Variations of the methods to produce the same compounds in somewhat different fashion will also be evident to one skilled in the art. To provide greater detail in description, representative synthetic examples are provided infra in the "Specific Embodiments" section.

Serotonin has been linked to the pathophysiology of migraine by accumulating evidence including increased excretion of serotonin metabolites following a migraine attack and a reduction in the serotonin content of blood platelets during the migraine headache. This latter effect appears to be specific for migraine and not a result of pain or stress. (Anthony, et al., "Plasma serotonin in migraine and stress", *Arch. Neurol.* 1967, 16: 544–552). More importantly, intramuscular injection of reserpine lowers plasma serotonin and induces a typical migraine-type headache in migraine sufferers. This induced headache can be alleviated by slow I.V. injection of serotonin creatinine sulfate. (Kimball, et al., "Effect of serotonin in migraine patients", *Neurology N.Y.*, 1960, 10: 107–111).

Although serotonin has been shown to be effective in treating migraine attacks, its use in migraine is precluded by its side-effects such as restlessness, nausea, faintness, hyperpnea, facial flushing and parasthesias. (Lance, et al., "The control of cranial arteries by humoral mechanisms and its relation to the migraine syndrome", *Headache*, 1967, 7: 93–102). For this reason more specific serotonin agents, which would treat the migraine without all of the other actions, are potentially useful antimigraine medicaments. Accumulating findings have led to the perception that compounds with selectivity for the 5-HT$_{1D}$ sub-type of serotonin receptors would be clinically efficacious in the treatment of migraine. In this regard the compounds of the instant invention demonstrate potent affinity and agonist activity at the 5-HT$_{1D}$ site. Formula I compounds of this invention have potencies wherein IC$_{50}$ values of these compounds are less than 100 nmolar. Preferred compounds have IC$_{50}$ values below 10 nmolar.

Determination of 5-HT$_{1D}$ binding properties was accomplished employing methodology such as that described by Heuring and Peroutka, *J. Neurosci.*, 7(3), 1987, 894–903; with only minor modifications. In vitro IC$_{50}$ (nM) test values were determined for the compounds of this invention employing tritiated serotonin.

In addition to the 5-HT$_{1D}$ binding test data, ability of the compounds of this invention to elicit contraction in a canine saphenous vein model further indicates usefulness in treating vascular headaches. Preferred compounds demonstrate potency equal to or in excess of serotonin itself. Selected compounds of the instant series were tested in an in vivo model where they demonstrated effective reduction of carotid blood flow in anesthetized dogs. All these foregoing pharmacologic tests indicate useful antimigraine action for the compounds of this invention.

Another aspect then of the instant invention provides a method for treating a migraine sufferer which comprises systemic administration to the sufferer of a therapeutically effective amount of a compound of Formula I or a pharmaceutically acceptable salt thereof.

The administration and dosage regimen of compounds of Formula I is considered to be done in the same manner as for the reference compound sumatriptan, cf: Oxford, GB 2,162, 522A. Although the dosage and dosage regimen must in each case be carefully adjusted, utilizing sound professional judgment and considering the age, weight and condition of the recipient, the route of administration and the nature and gravity of the illness, generally the daily dose will be from about 0.05 to about 10 mg/kg, preferably 0.1 to 2 mg/kg, when administered parenterally and from about 1 to about 50 mg/kg, preferably about 5 to 20 mg/kg, when administered orally. In some instances, a sufficient therapeutic effect can be obtained at lower doses while in others, larger doses will be required. Systemic administration refers to oral, intra-nasal, rectal and parenteral (i.e. intramuscular, intravenous and subcutaneous). Generally, it will be found that when a compound of the present invention is administered orally, a larger quantity of the active agent is required to produce the same effect as a smaller quantity given intranasally or parenterally. In accordance with good clinical practice, it is preferred to administer the instant compounds at a concentration level that will produce effective antimigraine effects without causing any harmful or untoward side effects.

The compounds of the present invention may be administered for antimigraine purposes either as individual therapeutic agents or as mixtures with other therapeutic agents. Therapeutically, they are generally given as pharmaceutical compositions comprised of an antimigraine amount of a compound of Formula I or a pharmaceutically acceptable salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g. starch) and wetting agents (e.g. sodium lauryl sulfate). Solutions or suspensions of a Formula I compound with conventional pharmaceutical vehicles are employed for intra-nasal and parenteral compositions such as an aqueous solution for intravenous injection or an oily suspension for intramuscular injection.

DESCRIPTION OF SPECIFIC EMBODIMENTS

The compounds which constitute this invention, their methods of preparation and their biologic actions will appear more fully from consideration of the following examples, which are given for the purpose of illustration only and are not be construed as limiting the invention in sphere or scope. In the following examples, used to illustrate the foregoing synthetic processes, temperatures are expressed in degrees Celsius and melting points are uncorrected. The nuclear magnetic resonance (NMR) spectral characteristics refer to chemical shifts ($\delta$) expressed as parts per million (ppm) versus tetramethylsilane (TMS) as reference standard. The relative area reported for the various shifts in the $^1$H NMR spectral data corresponds to the number of hydrogen atoms of a particular functional type in the molecule. The nature of the shifts as to multiplicity is reported as broad singlet (bs), singlet (s), multiplet (m), heptet (hept), quartet (q), triplet (t) or doublet (d). Abbreviations employed are DMSO-$d_6$ (deuterodimethyl-sulfoxide), CDCl$_3$ (deuterochloroform) and are otherwise conventional. The infrared (IR) spectral descriptions include only absorption wave numbers (cm$^{-1}$) having functional group identification value. The IR determinations were employed either neat or using potassium bromide (KBr) as diluent. The elemental analyses are reported as percent by weight.

The following examples describe in detail the preparation of compounds of Formula I, as well as synthetic intermediates in each process. It will be apparent to those skilled in the art that modifications, both of materials and methods, will allow preparation of other compounds disclosed herein. From the foregoing description and the following examples it is believed that one skilled in the art is able to use the invention to the fullest extent.

A. Preparation of Intermediate Compounds

Some representative procedures for preparation of synthetic intermediate compounds contained in the processes of the schemes are given hereinbelow. Most starting materials and certain intermediates (e.g. formula 1–3 and 8 compounds), are either commercially available or procedures for their synthesis are readily available in the chemical literature allowing their full utilization by one skilled in the art of organic synthetic chemistry.

Example 1

5-[(5-Nitro-1H-indol-3-yl)methyl]-2,2-dimethyl-1,3-dioxane-4,6-dione (17)

An adaption of the procedure of Flaugh[1] was used. Thus, a solution of 5-nitroindole (50.0 g, 0.32 mol), Meldrum's acid (46.0 g, 0.32 mol), 37% aqueous formaldehyde (26.0 mL, 0.32 mol) and proline (1.8 g, 0.016 mol) in 200 mL of acetonitrile was stirred at room temperature for 18 h. The resulting thick yellow slurry was filtered and the filtercake was washed with acetonitrile, then acetone and finally with ether. This material was dried in vacuo to give the title compound (80.0 g, 81%) as a bright yellow solid, mp 182° C. (dec). The mother liquor was concentrated and then diluted with H$_2$O, and the resulting solid was collected, washed and dried as before to give a second crop of the product (7.0 g) as a darker yellow solid. Total yield=87.0 g (89%): IR (KBr) 3330, 1767, 1732 cm$^{-1}$; $^1$H NMR (DMSO-$d_6$, 200 MHz) $\delta$ 11.64 (s, 1H), 8.63 (d, J=2.2 Hz, 1H), 7.96 (dd, J=9.0, 2.2 Hz, 1H), 7.49 (d, J=9.0 Hz, 1H), 7.33 (d, J=2.2 Hz, 1H), 4.84 (t, J=4.6 Hz, 1H), 3.45 (d, J=4.5 Hz, 2H), 1.78 (s, 3H), 1.55 (s, 3H). Anal. Calcd for C$_{15}$H$_{14}$N$_2$O$_6$: C, 56.60; H, 4.43; N, 8.80. Found: C, 56.62; H, 4.41; N, 8.91.

[1]. D. S. Farlow, M. E. Flaugh, S. D. Horvath, E. R. Lavignino, P. Pranc, *Org. Prep, Proc. Int.* 1981, 13, 39.

Example 2

Ethyl 5-nitro-3-(1H-indole)propionate

To a solution of [5-(5-nitroindol-3-yl)methyl]-2,2-dimethyl-1,3-dioxane-4,6-dione (10.0 g, 0.031 mol) in a mixture of pyridine (80 mL) and absolute ethanol (20 mL) was added 0.1 g of copper powder and the mixture was heated to reflux under Ar for 2 h. The cooled mixture was filtered and the filtrate was evaporated. The resulting residue was triturated with ether-dichloromethane to give the title compound (7.3 g, 89%) as a solid, mp 118°–121° C.: IR (KBr) 3330, 1730 cm$^{-1}$; $^1$H NMR (DMSO-$d_6$, 200 MHz) $\delta$ 11.59 (br s, 1H), 8.53 (d, J=2.2 Hz, 1H), 7.97 (dd, J=9.0, 2.3 Hz, 1H), 7.49 (d, J=9.0 Hz, 1H), 7.40 (d, J=2.1 Hz, 1H), 4.03 (q, J=7.1 Hz, 2H), 3.02 (t, J=7.4 Hz, 2H), 2.67 (t, J=7.4 Hz, 2H), 1.13 (t, J=7.1 Hz, 3H).

Example 3

5-Nitro-3-(3-hydroxypropyl)-1H-indole (18)

To a suspension of 95% LiAlH$_4$ (2.20 g, 0.058 mol) in 60 mL of dry THF was added a solution of ethyl 5-nitro-3-indolepropionate (7.30 g, 0.028 mol) in 100 mL of dry THF, at 0° C. under Ar. After stirring for 20 min, the mixture was quenched by the cautious addition of 3 mL of H$_2$O. The resulting suspension was stirred for 10 min and then it was filtered and the filtercake was washed with additional THF. The filtrate was evaporated and the residue was taken up in ether, dried (Na$_2$SO$_4$) and evaporated, and the resulting solid was triturated with hexane to give the title compound (4.30 g, 70%) as a yellow solid, mp 107°–110° C.: IR (KBr) 3480, 3180, 1625 cm$^{-1}$; $^1$H NMR (CDCl$_3$, 200 MHz) $\delta$ 8.60 (d, J=2.1 Hz, 1H), 8.35 (br s, 1H), 8.11 (dd, J=9.0, 2.2 Hz, 1H), 7.38 (d, J=8.9 Hz, 1H), 7.16 (m, 1H), 3.75 (t, J=6.2 Hz, 2H), 2.91 (t, J=7.2 Hz, 2H), 2.07–1.93 (m, 2H), 1.37 (br s, 1H).

Example 4a 3-(3-Bromopropyl)-5-nitro-1H-indole (4)

To a solution of triphenylphosphine (6.70 g, 0.025 mol) in 80 mL of acetonitrile was added a solution of 5-nitro-3-(3-hydroxypropyl)indole (18) (4.30 g, 0.020 mol) in 75 mL of acetonitrile, followed by a solution of CBr$_4$ (9.00 g, 0.027 mol) in 25 mL of acetonitrile, at 0° C. under Ar. The mixture was stirred at room temperature for 3 h and then it was evaporated and the residue was chromatographed (SiO$_2$/ethyl acetate-hexane, 1:9 then 1:4) to give the title compound (4.60 g, 84%) as a solid, mp 92°–95° C.: IR (neat) 3420, 1330 cm$^{-1}$; $^1$H NMR (CDCl$_3$, 200 MHz) $\delta$ 8.59 (d, J=2.1 Hz, 1H), 8.40 (br s, 1H), 8.13 (dd, J=9.0, 2.2 Hz, 1H), 7.40 (d, J=9.1 Hz, 1H), 7.21 (d, J=2.2 Hz, 1H), 3.45 (t, J=6.4 Hz, 2H), 2.99 (t, J=7.2 Hz, 2H), 2.26 (m, 2H).

Example 4b

3-[3-Iodopropyl]-5-nitro-1H-indole. (4)

A solution of 3-[3-hydroxypropyl]-5-nitro-1H-indole (18) (1.13 g, 5.06 mmol) in 20 mL of acetonitrile was cooled to 0° C. and treated sequentially with triethylamine (1.05 mL, 7.59 mmol) and methanesulfonyl chloride (0.43 mL, 5.6 mmoL) and the mixture stirred for 30 min. The reaction mixture was quenched with 30 mL of water and the organic material was extracted into ethyl acetate. The organic extracts were dried ($MgSO_4$) and concentrated in vacuo. The crude residue was dissolved in 20 mL of acetonitrile containing KI (1.7 g, 10.1 mmol) and heated to reflux for 3 h. The reaction mixture was cooled and the solvent removed in vacuo. The residue was dissolved in 100 mL of ethyl acetate and washed with water. The ethyl acetate layer was dried ($MgSO_4$) and concentrated and the residue was purified by flash column chromatography (20% ethyl acetate in hexanes) to give the title compound 1.37 g, 4.20 mmol, 83%) as a yellow solid: mp 95°–98° C.; $^1$H NMR (DMSO-$d_6$, 300 MHz) δ 8.53 (d, J=2.3 Hz, 1H), 7.97 (dd, J=2.3, 9.0 Hz, 1H), 7.51 (d, J=9.0 Hz, 1H) 7.43 (s, 1H), 3.30 (t, J=6.7 Hz, 2H), 2.84 (t, J=7.7 Hz, 2H), 2.11 (m, 2H); IR (KBr) 1330, 1510, 810 cm$^{-1}$; MS (m/e) 330 (M$^+$). Anal. Calcd for $C_{11}H_{11}IN_2O_2$: C, 40.02, H 3.36, N 8.48. Found: C, 40.26; H, 3.27; N, 8.51.

Example 5a

3-[3-[4-(5-Methoxy-4-pyrimidyl)-1-piperazinyl]propyl]-5-nitro-1H-indole (5)

A mixture of 5-nitro-3-(3-bromopropyl)indole (4) (0.57 g, 2.0 mmol), 1-(5-methoxy-4-pyrimidyl)piperazine, (1) (0.47 g, 2.4 retool), KI (0.40 g, 2.4 mmol) and diisopropylethylamine (1.75 mL, 10.0 mmol) in 20 mL of acetonitrile was heated to reflux under Ar for 6 h. The cooled reaction mixture was diluted with ethyl acetate and washed ($H_2O$, brine). The aqueous phase was back-extracted with dichloromethane and the combined organic phase was washed ($H_2O$, brine), dried ($Na_2SO_4$) and evaporated. The resulting residue was chromatographed ($SiO_2/CH_2Cl_2$-MeOH, 95:5) to give a solid which was triturated with dichloromethane-hexane to afford the title compound (0.55 g, 70%) as a yellow solid, mp 163°–166° C.: IR (KBr) 3440, 3175, 1578, 1320 cm$^{-1}$; $^1$H NMR (CDCl$_3$, 200 MHz) δ 8.60 (d, J=2.1 Hz, 1H), 8.47 (br s, 1H), 8.33(s, 1H), 8.11 (dd, J=9.0, 2.2 Hz, 1H), 7.89 (s, 1H), 7.38 (d, J=9.0 Hz, 1H), 7.18 (d, J=2.0 Hz, 1H), 3.86 (s, 3H), 3.8–3.9 (m, 4H), 2.86 (t, J=7.4 Hz, 2H), 2.59 (t, J=4.9 Hz, 4H), 2.50 (t, J=7.5 Hz, 2H), 2.05–1.90 (m, 2H). *Anal. Calcd* for $C_{20}H_{24}N_6O_3 \cdot H_2O \cdot 0.1\ CH_2Cl_2$: C, 57.08; H, 6.24; N, 19.87. Found: C, 57.37; H, 5.85; N, 19.53.

Example 5b

3-[3-[4-(3-Methoxy-4-pyridinyl)-1-piperazinyl]propyl]-5-nitro-1H-indole. (5)

A mixture of 3-[3-iodopropyl]-5-nitro-1H-indole (4) (1.4 g, 4.2 mmol), 1-(3-methoxy-4-pyridinyl)-1-piperazine (1) (0.98 g, 5.09 mmol) and $K_2CO_3$ (1.4 g, 10.2 mmol) in 30 mL of acetonitrile was heated to reflux for 4 h. The reaction mixture was cooled and stirred for 12 h. The solvent was removed and the residue dissolved in ethyl acetate and water. The aqueous layer was separated and extracted with ethyl acetate. The organic extracts were dried ($MgSO_4$) and concentrated, and the gummy residue was purified by flash silica gel chromatography (5% methanol in dichloromethane as eluant) to give 3-[3-[4-(3-methoxy-4-pyridinyl)-1-piperazinyl]propyl]-5-nitro-1H-indole, (0.6 g, 36%) as a yellow solid: $^1$H NMR (DMSO-$d_6$, 300 MHz) δ 8.52 (d, J=2.2 Hz, 1H), 8.10 (s, 1H), 8.02 (d, J=5.3 Hz, 1H), 7.96 (dd, J=2.3, 9.0 Hz, 1H), 7.48 (d, J=9.0 Hz, 1H), 7.42 (s, 1H), 6.81 (d, J=5.4 Hz, 1H), 3.84 (s, 3H), 3.21 (br s, 4H), 3.07 (dd, J=6.4, 14.7 Hz, 2H), 2.79 (t, J=14.7 Hz, 2 H) , 2.66 (br s, 4H), 1.97 (m, 2H); IR (KBr) 3600, 2400, 1600, 1520, 1330, 1250, 815 cm$^{-1}$; MS (m/e) 395 (M$^+$).

Example 5c

3-[3-[4-(2-Pyridinyl)-1-piperazinyl]propyl]-5-nitro-1H-indole. (5)

A mixture of 3-[3-bromopropyl]-5-nitro-1H-indole (4) (1.4 g, 4.2 mmol), 1-(2-pyridinyl)-piperazine, (1) (0.98 g, 5.09 mmol) and $K_2CO_3$ (1.4 g, 10.2 mmol) in 30 mL of acetonitrile was heated to reflux for 4 h. The reaction mixture was cooled, the solvent was removed and the residue dissolved in ethyl acetate and water. The aqueous layer was separated and extracted with ethyl acetate. The organic extracts were dried ($MgSO_4$) and concentrated, and the gummy residue purified by flash silica gel chromatography (5% methanol in dichloromethane) to give 3-[3-[4-(2-pyridinyl)-1-piperazinyl]propyl]-5-nitro-1H-indole, (0.6 g, 36%) as a yellow solid: $^1$H NMR (DMSO-$d_6$, 300 MHz) δ 8.52 (d, J=2.24 Hz, 1H), 8.80 (dd, J=1.8, 4.8 Hz, 1H), 7.95 (dd, J=2.25, 9.0 Hz, 1H), 7.52–7.49 (m, 2H), 7.41 (s, 1H), 6.79 (d, J=8.6 Hz, 1H), 6.60 (t, J=6.6 Hz, 1H), 3.46 (t, J=4.7 Hz, 4H), 2.78 (t, J=7.4 Hz, 2H), 2.42 (t, J=5.0 Hz, 4H), 2.34 (t, J=6.9 HZ, 4H), 1.82 (dt, J=7.4, 6.9 Hz, 2H); IR(KBr) 3182, 1520, 1330 cm$^{-1}$; MS (m/e) 365 (M$^+$). Anal. Calcd for $C_{20}H_{23}N_5O_2$: C, 65.73, H, 6.34, N 19.16; found C, 65.35, H, 6.26, N, 18.87.

Example 5d

3-[3-[(3-Methoxy-2-pyridinyl)-1-piperazinyl]propyl]-5-nitro-1H-indole. (5)

A mixture of 3-(3-bromopropyl)-5-nitro-1H-indole (4) (0.88 g, 3.11 mmol), potassium carbonate (0.43 g, 3.11 mmol), potassium iodide (0.52 g, 3.11 mmol) and 1-(3-methoxy-2-pyridinyl)piperazine (1) (0.60 g, 3.11 mmol) in 50 mL of acetonitrile was heated to reflux for 5 h. The mixture was cooled, filtered and concentrated. The residue was purified by flash column chromatography with 5% methanol in dichloromethane as eluant to give the title compound (1.2 g, 99%) as a yellow foam; $^1$H NMR (DMSO-$d_6$, 300 MHZ) δ 8.54 (d, J=2.2 Hz, 1H), 7.97 (dd, J=2.2, 9.9 Hz, 1H), 7.77(m, 1H), 7.50 (d, J=9.0 Hz, 1H), 7.44 (s, 1H), 7.24 (d, J=7.75 Hz, 1H), 6.90 (m, 1H), 3.78 (s, 3H), 3.33 (br s, 2H), 2.80 (t, J=7.3 Hz, 2H), 1.93 (m, 2H); IR(KBr) 3300, 1520, 1330, 1240 cm$^{-1}$; MS (m/e) 395 (M$^+$).

Example 6

3-[3-[4-(5-Methoxy-4-pyrimidyl)-1-piperazinyl]propyl]-5-amino-1H-indole (6)

To a solution of 3-[3-[4-(5-methoxy-4-pyrimidyl)-1-piperazinyl]propyl]-5-nitroindole(5) (0.550 g, 1.39 mmol) in a mixture of ethanol (120 mL) and THF (40 mL) was added 10% palladium-on-charcoal (0.30 g) and the mixture was hydrogenated on a Parr shaker at 40 psi for 18 h. The mixture was then filtered through Celite and the catalyst was washed with additional ethanol-THF. Evaporation of the filtrate gave the essentially pure title compound (0.557 g, 100%) as a brown foam. A sample of this material (0.143 g) was treated with excess methanolic HCl and the resulting solution was diluted with acetone to give a precipitate. The precipitate was filtered and then crystallized from ethanol to give 0.100 g of a purplish solid, mp 192° C. (dec): IR (KBr) 3410, 3200, 1630, 1540 cm$^{-1}$; $^1$H NMR (DMSO-d$_6$, 200 MHz) δ 11.22(br s, 1H), 10.20 (br s, 2H), 8.60 (m, 1H), 8.20 (s, 1H), 7.55 (d, J=1.6 Hz, 1H), 7.45 (d, J=8.6 Hz, 1H), 7.35 (d, J=2.1 Hz, 1H), 7.07 (dd, J=8.6, 1.9 Hz, 1H), 4.89–4.82 (m, 2H), 3.91 (s, 3H), 3.8–3.0 (br m, 8H), 2.76 (m, 2). Anal. Calcd for C$_{20}$H$_{26}$N$_6$O. 4 HCl. H$_2$O: C, 45.29; H, 6.08; N, 15.85. Found: C, 45.32; H, 5.97; N, 15.59.

Example 7

5-Bromo-3-(3-hydroxypropyl)-1H-indole (9)

A modification of a procedure reported by Grandberg (Chem. Abstr. 1973, 79,918895) was used. Thus, to a suspension of 4-bromophenylhydrazine hydrochloride (56.0 g, 0.25 mol) in 200 mL of 2-methoxyethanol was added 3,4-dihydro-2H-pyran (25.5 mL, 0.28 mol) over ca. 5 min and the resulting mixture was heated to reflux under Ar for 3.5 h. The cooled reaction mixture was evaporated and the residual oil was poured into 500 mL of cold water. The aqueous mixture was extracted with ether (2×250 mL) and the ethereal extract was washed with H$_2$O (250 mL), 1N HCl (2×250 mL) and brine (250 mL). The organic phase was then dried (Na$_2$SO$_4$) and evaporated to give a dark orange-brown oil. This oil was purified on a 10×15 cm SiO$_2$ pad (elution with CH$_2$Cl$_2$ then CH$_2$Cl$_2$-ethyl acetate, 1:1) to give the title compound (43.7 g, 69%) as a viscous orange-brown oil: IR (neat) 3570, 3430, 3300 (br), 1460 cm$^{-1}$; $^1$H NMR (CDCl$_3$, 200 MHz) δ 0.11 (br s, 1H), 7.73 (d, J=1.8 Hz, 1H), 7.30–7.18 (m, 2H), 6.97 (s, 1H), 3.72 (t, J=6.4 Hz, 2H), 2.80 (t, J=7.5 Hz, 2H), 2.03–1.89 (m, 2H), 1.68 (br s, 1H).

Example 8

5-Bromo-3-(3-triisopropylsiloxypropyl)-1-triisopropyl-silyl-1H-indole (10)

To an ice-cold suspension of sodium hydride (80% in oil, 1.92 g, 0.064 mol) in 150 mL of DMF was added 5-bromo-3-(3-hydroxypropyl)indole (9) (7.40 g, 0.029 mol) portionwise over 5 min. The resulting dark brown mixture was stirred at 0° C. for 15 min and then the cooling bath was removed and stirring was continued at room temperature for 1.5 h. The mixture was then recooled at 0° C. and triisopropylsilyl chloride (15.0 mL, 0.070 mol) was added. After being kept at 0° C. for 15 min and then at room temperature for 18 h, the mixture was quenched with 10 mL of saturated aqueous NH$_4$Cl and then it was poured into 200 mL of water and extracted with ether (3×150 mL). The organic phase was washed (10% sat. NaHCO$_3$, H$_2$O, brine), dried (Na$_2$SO$_4$) and evaporated to give a brown oil. This material was filtered through a pad of SiO$_2$ (elution with hexane then hexane-CH$_2$Cl$_2$, 9:1) to give the title compound (14.10 g, 86%) as a colourless, viscous oil: IR (neat) 1443, 1110 cm$_{-1}$; $^1$H NMR (CDCl$_3$, 200 MHz) δ 7.69 (d, J=1.9 Hz, 1H), 7.32 (d, J=8.8 Hz, 1H), 7.19 (dd, J=8.8, 1.9 Hz, 1H), 7.00 (s, 1H), 3.73 (t, J=6.4 Hz, 2H), 2.79 (t, J=7.4 Hz, 2H), 1.99–1.85 (m, 2H), 1.65 (hept, 7.6 Hz, 3H), 1.26–1.00 (m, 39H).

Example 9

5-[1,2-Dioxo-4-(1-methylethoxy)-3-cyclobuten-3-yl]-3-(3-triisopropysiloxypropyl)-1-triisopropylsilyl-1H-indole (11)

To a solution of 5-bromo-3-(3-triisopropylsiloxy-propyl)-1-triisopropylsilylindole 10) (5.66 g, 0.010 mol) in 50 mL of anhydrous ether, cooled at −78° C. under Ar, was added a solution of t-butyllithium (1.7M in pentane, 12.9 mL, 0.022 mol) dropwise over 10 min. After 30 min at −78° C., a solution of 3,4-bis(1-methylethoxy)cyclobut-3-ene-1,2-dione[2] (1.98 g, 0.010 mol) in 10 mL of anhydrous ether was slowly added. The mixture was stirred at −78° C. for another 30 min and then it was quenched with 2 mL of saturated aqueous NH$_4$Cl and poured into water. The organic phase was separated and then it was washed (H$_2$O, brine), dried (Na$_2$SO$_4$) and evaporated to give an orange-yellow gum. This gum was taken up in 75 mL of dichloromethane, 10 drops of conc. HCl were added and the mixture was vigorously stirred at room temperature for 1 h. The resulting mixture was washed with saturated aqueous NaHCO$_3$, dried (Na$_2$SO$_4$) and evaporated to give a brown gum. Flash chromatography (SiO$_2$/pet. ether-CH$_2$Cl$_2$, 9:1) of this gum afforded the title compound (2.98 g, 48%) as a foam: IR (neat) 1782, 1740, 1587, 1387, 1095 cm$^{-1}$; $^1$H NMR (CDCl$_3$, 200 MHz) δ 8.39 (d, J=1.6 Hz, 1H), 7.84 (dd, J=8.7, 1.7 Hz, 1H), 7.55 (d, J=8.7 Hz, 1H), 7.08 (s, 1H), 5.63 (hept, J=6.2 Hz, 1H), 3.76 (t, J=6.5 Hz, 2H), 2.88 (t, J=7.5 Hz, 2H), 2.05–1.91 (m, 2H), 1.69 (hept, J=7.5 Hz, 3H), 1.55 (d, J=6.2 Hz, 6H), 1.16–1.02 (m, 39H).

[2]. L. S. Liebeskind, et al, *J. Org. Chem.* 1988, 53/2482.

Example 10

5-[1,2-Dioxo-4-(1-methylethoxy)-3-cyclobuten-3-yl]-3-(3-hydroxypropyl)-1-triisopropylsilyl-1H-indole (12)

To a solution of 5-[1,2-dioxo-4-(1-methylethoxy)-3-cyclobuten-3-yl]-3-(3-triisopropylsiloxypropyl)-1-triisopropylsilylindole (11) (0.315 g, 0.50 mmol) in 5 mL of acetonitrile was added 48% HF (10% in MeCN, 0.35 mL, 1.0 mmol) and the mixture was stirred at room temperature for 30 min. The reaction was then quenched with 10% aqueous Na$_2$CO$_3$, ethyl acetate was added and the mixture was washed (10% aq. Na$_2$CO$_3$, brine), dried (Na$_2$SO$_4$) and evaporated to give a yellow gum. Flash chromatography (SiO$_2$/hexane-ethyl acetate, 1:1) of this gum afforded the title compound (0.209 g, 89%) as a yellow foam: IR (neat) 3480 (br), 1782, 1735, 1585, 1390 cm$^-$; $^1$H NMR (CDCl$_3$, 200 MHz) δ 8.43 (d, J=1.4 Hz, 1H), 7.82 (dd, J=8.7, 1.7 Hz, 1H), 7.56 (d, J=8.7 Hz, 1H), 7.10 (s, 1H), 5.64 (hept, J=6.2 Hz, 1H), 3.74 (t, J=6.4 Hz, 2H), 2.90 (t, J=7.4 Hz, 2H), 2.09–1.95 (m, 2H), 1.69 (hept, J=7.5 Hz, 3H), 1.57 (d, J=6.2 Hz, 6H), 1.14 (d, J=7.5 Hz, 18H).

Example 11

5-[1,2-Dioxo-4-(1-methylethoxy)-3-cyclobuten-3-yl]-3-[3-(p-toluenesulfonyl)oxy-propyl]-1-triisopropylsilyl-1H-indole (13)

To an ice-cold solution of 5-[1,2-dioxo-4-(1-methylethoxy)-3-cyclobuten-3-yl]-3-(3-hydroxypropyl]-1-triisopropylsilylindole (12) (0.208 g, 0.44 mmol) in 5 mL of dichloromethane was added p-toluenesulfonyl chloride (0.094 g, 0.49 mmol), followed by triethylamine (68 μL, 0.49 mmol) and a small but arbitrary amount of 4-dimethylaminopyridine. The cooling bath was then removed and the mixture was stirred at room temperature under Ar for 1 h. Another 0.047 g (0.25 mmol) of p-toluenesulfonyl chloride and 34 μL (0.24 mmol) of triethylamine were added and stirring was continued at room temperature for 18 h. The mixture was then diluted with dichloromethane, washed with 10% aqueous $Na_2CO_3$, dried ($Na_2SO_4$) and evaporated to give a yellow gum. Flash chromatography ($SiO_2/CH_2Cl_2$ then hexane-ethyl acetate, 1:1) of this material afforded the title compound (0.265 g, 97%) as a bright yellow gum: IR (neat) 1782, 1738, 1585, 1390 cm$^{-1}$; $^1$H NMR (CDCl$_3$, 400 MHz) δ 8.34 (d, J=1.5 Hz, 1H), 7.81 (dd, J=8.7, 1.5 Hz, 1H), 7.79 (d, J=8.3 Hz, 2H), 7.56 (d, J=8.7 Hz, 1H), 7.33 (d, J=8.0 Hz, 2H), 7.10 (s, 1H), 5.64 (hept, J=6.2 Hz, 1H), 4.09 (t, J=7.2 Hz, 2H), 2.87 (t, J=7.3 Hz, 2H), 2.44 (s, 3H), 2.11–2.05 (m, 2H), 1.70 (hept, J=7.5 Hz, 3H), 1.58 (d, J=6.1 Hz, 6H), 1.14 (d, J=7.5 Hz, 18H).

Example 12

5-[1,2-Dioxo-4-methylamino-3-cyclobuten-3-yl]-3-[3-(p-toluenesulfonyl)oxypropyl]-1-triisopropylsilyl-1H-indole (14)

Anhydrous methylamine was bubbled into 7 mL of absolute ethanol at 0° C. for ca. 15 min. To this cold solution was added a solution of 5-[1,2-dioxo-4-(1-methylethoxy)-3-cyclobuten-3-yl]-3-[3-(p-toluenesulfonyl)oxypropyl]-1-triisopropylsilylindole (13) (0.262 g, 0.42 mmol) in 2 mL of dichloromethane and the resulting solution was stirred at 0° C. for 15 min. The reaction mixture was then evaporated to give the essentially pure title compound (0.250 g, 100%) as a light yellow foam. This material was used in the next step without further purification: IR (neat) 3260 (br), 3180 (br), 1771, 1720, 1607, 1398, 1178 cm$^{-1}$; $^1$H NMR (CDCl$_3$, 200 MHz) δ 8.00 (m, 1H), 7.84 (s, 1H), 7.77 (d, J=8.4 Hz, 2H), 7.55 (d, J=8.7 Hz, 1H), 7.34 (d, J=8.1 Hz, 2H), 7.08 (s, 1H), 6.70 (br m, 1H), 4.12 (t, J=5.7 Hz, 2H), 3.50 (d, J=5.0 Hz, 3H), 2.93 (m, 2H), 2.45 (s, 3H), 2.08 (m, 2H), 1.67 (hept, J=7.5 Hz, 3H), 1.12 (d, J=7.5 Hz, 18H).

Examples 13–15

In a manner similar to Example 12, substituting ammonia or isopropylamine or t-butylamine for methylamine and reaction with the compound of Example 11 afforded Examples 13, 14 and 15, respectively:

Example 13

5-[1,2-Dioxo-4-amino-3-cyclobuten-3-yl-]-3-[3-(p-toluene sulfonyl)oxypropyl]-1-triisopropylsilyl-1H-indole (14)

IR (neat) 3325 (br), 3205 (br), 1778, 1720, 1640, 1570, 1405 cm$^{-1}$; $^1$H NMR (CDCl$_3$, 400 MHz) 6 7.98 (d, J=1.4 Hz, 1H), 7.95 (dd, J=8.7, 1.4 Hz, 1H), 7.78 (d, J=8.3 Hz, 2H), 7.58 (d, J=8.7 Hz, 1H), 7.34 (d, J=8.0 Hz, 2H), 7.10 (s, 1H), 6.53 (br s, 2H), 4.14 (t, J=5.8 Hz, 2H), 2.93 (t, J=7.2 Hz, 2H), 2.45 (s, 3H), 2.13–2.07 (m, 2H), 1.69 (hept, J=7.6 Hz, 3H), 1.14 (d, J=7.5 Hz, 18H).

Example 14

5-[1,2-Dioxo-4-isopropylamino-3-cyclobuten-3yl]-3-[3-(p-toluenesulfonyl)oxyprop-yl]-1-triisopropylsilyl-1H-indole (14)

IR (neat) 3285 (br), 1770, 1718, 1590 (br) cm$^{-1}$; $^1$H NMR (CDCl$_3$, 200 MHz) δ 8.00 (d, J=1.6 Hz, 1H), 7.84 (m, 1H), 7.76 (d, J=8.3 Hz, 2H), 7.56 (d, J=8.7 Hz, 1H), 7.33 (d, J=7.1 Hz, 2H), 7.08 (s, 1H), 6.40 (m, 1H), 4.72 (m, 1H), 4.11 (t, J=5.9 Hz, 2H), 2.93 (t, J=7.0 Hz, 2H), 2.44 (s, 3H), 2.11 (m, 2H), 1.67 (hept, J=7.5 Hz, 3H), 1.35 (d, J=6.6 Hz, 6H), 1.13 (d, J=7.5 Hz, 18H).

Example 15

5-[1,2-Dioxo-4-t-butylamino-3-cyclobuten-3-yl]-3-[3-(p-toluenesulfonyl)oxypropyl]-1-triisopropylsilyl-1H-indole (14)

IR (neat) 3330 (br), 1767, 1717, 1570 (br) cm$^{-1}$; $^1$H NMR (CDCl$_3$, 200 MHz) δ 8.11 (s, 1H), 7.74 (d, J=8.2 Hz, 2H), 7.55 (m, 2H), 7.31 (d, J=8.2 Hz, 2H), 7.10 (s, 1H), 6.26 (s, 1H), 4.06 (t, J=6.1 Hz, 2H), 2.88 (t, J=7.5 Hz, 2H), 2.42 (s, 3H), 2.08 (m, 2H), 1.68 (hept, J=7.5 Hz, 3H), 1.59 (s, 9H), 1.13 (d, J=7.5 Hz, 18H).

B. Indolyl-Amino-Squarate Compounds
1. Formula I-1 Products

Example 16

3-[3-[4-(5-Methoxy-4-pyrimidinyl)-1-piperazinyl] propyl]-5-[(1,2-dioxo-4-methyl-3-cyclobuten-3-yl)aminomethyl]indole.

A. 5-Aminomethyl-3-(3-hydroxypropyl)indole (19)

To a solution of 5-cyano-3-(3-hydroxypropyl)indole (1.00 g, 0.005 mol) in 30 mL of absolute ethanol was added 10% palladium-on-charcoal (1.00 g) and the mixture was hydrogenated on a Parr shaker at 40 psi for 6 h. The mixture was then filtered, through Celite, the filtercake was washed with additional ethanol and the filtrate was evaporated to give a colourless gum. Flash chromatography ($SiO_2$/MeCN—MeOH, 9:1 then MeCN—MeOH—NH$_4$OH, 90:9:1) afforded the essentially pure title compound (0.67 g, 70%) as a colourless gum: IR (neat) 3250 cm$^{-1}$; $^1$H NMR (DMSO-d$_6$, 200 MHz) δ 10.60 (s, 1H), 7.41 (s, 1H), 7.23 (d, J=8.2 Hz, 1H), 7.04 (s, 1H), 7.02 (d, J=8.1 Hz, 1H), 4.4 (br s, 1H), 3.75 (s, 2H), 3.46 (t, J=6.5 Hz, 2H), 3.3 (br s, 2H), 2.68 (m, 2H), 1.78 (m, 2H).

B. 5-(1,2-Dioxo-4-methyl-3-cyclobuten-3-yl)aminomethyl-3-(3-hydroxypropyl)indole (20)

To a solution of 5-aminomethyl-3-(3-hydroxypropyl)indole (0.65 g, 0.0032 mol) in 12 mL of absolute ethanol was added 3-(1-methylethoxy)-4-methylcyclobut-3-ene-1,2-dione[3] (0.56 g, 0. 0036 mol) and the mixture was stirred at room temperature under Ar for 20 h. Evaporation of the resulting mixture gave a brown gum which was chromatographed ($SiO_2/CH_2Cl_2$ the $CH_2Cl_2$—MeOH, 95:5) to give the title compound (0.49 g, 51%) as an off-white foam: IR (neat) 3300 (br), 1785, 1720, 1600 (br) cm$^{-1}$; $^1$H NMR (DMSO-d$_6$, 200 MHz) δ 10.75 (s, 1H), 9.45 (m, 0.3H), 9.18 (m, 0.7H), 7.44 (s, 1H), 7.33 (d, J=8.4 Hz, 1H), 7.10 (s, 1H), 6.98 (d, J=8.4 Hz, 1H), 4.77 (s, 1H), 4.61 (m, 1H), 4.42 (m, 1H), 3.43 (m, 2H), 2.68 (m, 2H), 2.14 (s, 1.2H), 2.05 (s, 1.8H), 1.77 (m, 2H).

[3]. Cf: footnote 2. in Example 9.

C. 5-(1,2-Dioxo-4-methyl-3-cyclobuten-3-yl)aminomethyl-3-(3-methanesulfonyloxypropyl)indole (21)

To a solution of 5-(1,2-dioxo-4-methyl-3-cyclobuten-3-yl)aminomethyl-3-(3-hydroxypropyl)indole (0.48 g, 0.0016 mol) in 45 mL of dichloromethane-THF (4:1), cooled at −20° C. under Ar, was added triethylamine (0.28 mL, 0.002 mol) followed by methanesulfonyl chloride (0.16 mL, 0.002 mol). The resulting solution was stirred at −20° C. for 1.5 h and then it was washed (brine), dried ($Na_2SO_4$) and evaporated to give a brown gum. This material was chromatographed ($SiO_2$/ethyl acetate) to give the title compound (0.50 g, 83%) as a beige foam: IR (neat) 3320 (br), 1785, 1727, 1600 (br), 1350 (br) $cm^{-1}$; $^1H$ NMR (DMSO-$d_6$, 200 MHz) δ 10.86 (s, 1H), 9.45 (m, 0.5H), 9.21 (m, 0.5H), 7.48 (s, 1H), 7.33 (d, J=8.3 Hz, 1H), 7.17 (s, 1H), 7.03 (d, J=8.3 Hz, 1H), 4.78 (d, J=5.9 Hz, 1.2H), 4.62 (d, J=6.0 Hz, 0.8H), 4.23 (m, 2H), 3.80 (s, 3H), 3.06 (m, 2H), 2.76 (m, 2H), 2.14 (s, 1.2H), 2.05 (s, 1.8H).

D. 3-[3-[4-(5-Methoxy-4-pyrimidyl)-1-piperazinyl-propyl]-5-[(1,2-dioxo-4-methyl-3-cyclobuten-3-yl)aminomethyl]indole (I-1)

A mixture of 5-(1,2-dioxo-4-methyl-3-cyclobuten-3-yl)aminomethyl-3-(3-methanesulfonyloxypropyl)indole (21) (0.500 g, 1.33 mmol), 1-(5-methoxy-4-pyrimidyl)-piperazine (0.285 g, 1.47 mmol), finely pulverized KI (0.244 g, 1.47 mmol) and diisopropylethylamine (1.20 mL, 6.9 mmol) in 10 mL of acetonitrile was heated to reflux under Ar for 4 h. The resulting mixture was diluted with ethyl acetate, washed ($H_2O$, brine), dried ($Na_2SO_4$) and evaporated to give a beige foam. Flash chromatography ($SiO_2/CH_2Cl_2$—MeOH—$NH_4OH$, 90:9:1) afforded the title compound (0.570 g, 90%) as a foam. This material was taken up in excess methanolic HCl, the resulting solution was evaporated and the residue was triturated with acetone to give a solid. Recrystallization from methanol-acetone gave the hydrochloride (0.220 g, 27%) as an off-white solid, mp 95° C. (foams): IR (KBr) 3420 (br), 3230 (br), 1785, 1720, 1605 $cm^{-1}$; $^1H$ NMR (DMSO-$d_6$, 200 MHz) δ 11.1 (br s, 1H), 10.92 (s, 1H), 9.49 (m, 0.3H), 9.32 (m, 0.7H), 8.60 (s, 1H), 8.20 (s, 1H), 7.49 (m, 1H), 7.35 (d, J=8.3 Hz, 1H), 7.22 (s, 1H), 7.05 (d, J=8.3 Hz, 1H), 4.89–4.77 (m, 3H), 4.64 (d, J=6.0 Hz, 1H), 3.90 (s, 3H), 3.61 (br m, 6H), 3.13 (m, 4H), 2.75 (m, 2H), 2.14 (s, 1H), 2.07 (s, 2H). Anal. Calcd for $C_{26}H_{30}N_6O_3$·3 HCl.2.2 $H_2O$: C, 50.08; H, 6.05; N, 13.48. Found: C, 49.84; H, 5.80; N, 13.71.

Example 17

3-[3-[4-(5-Methoxy-4-pyrimidyl)-1-piperazinyl]propyl]-5-(1,2-dioxo-4-methyl-3-cyclobuten-3-yl)amino-1H-indole (I-1)

A solution of 3-[3-[4-(5-methoxy-4-pyrimidyl)-1-piperazinyl]propyl]-5-aminoindole (6) (0.190 g, 0.52 mmol) and 3-(1-methylethoxy)-4-methylcyclobut-3-ene-1,2-dione (3) (0.080 g, 0.52 mmol) in 1 mL of dry DMF was stirred at room temperature for 66 h and then it was heated at 130° C. (oil-bath temperature) for 6 h. The cooled mixture was evaporated and the residue was chromatographed (SiO2/$CH_2Cl_2$—MeOH, 95:5 then $CH_2Cl_2$—MeOH—$NH_4OH$, 95:4.5:0.5 to 90:9:1) to give the title compound (0.138 g, 58%) as a brown foam. This material was treated with excess methanolic HCl, the resulting solution was evaporated and the residue was triturated with isopropanol to give the hydrochloride 0.140 g, 45%) as a solid, mp 200° C. (dec): IR (KBr) 3400, 3220, 1782, 1630, 1600 $cm^{-1}$; $^1H$ NMR (DMSO-$d_6$, 200 MHz) δ11.08–10.83 (m, 2H), 8.59 (s, 1H), 8.19 (s, 1H), 7.57–7.04 (m, 4H), 4.85 (m, 2H), 3.90 (s, 3H), 2.8–2.4 (m, 8H), 3,13 (m, 2H), 2.26 (s, 1.5H), 2.10 (m, 2H), 1.89 (s, 1.5H). Anal. Calcd for $C_{25}H_{28}N_6O_3$. 3 HCl 0.75 $H_2O$. 0.25 $C_3H_8O$: C, 51.68; H, 5.81; N, 14.04. Found: C, 51.43; H, 5.61; N, 13.93.

Examples 18, 19 and 20 were prepared in a similar manner by reduction of Examples 5b, 5c and 5d according to the procedure of Example 6 and subsequently reacted with 3-(1-methylethoxy)-4-methylcyclobut-3-ene-1,2-dione as in Example 17.

Example 18

3-[[3-[3-[4-(3-Methoxy-4-pyridinyl)-1-piperazinyl] propyl]-1H-indol-5-yl]amino]-4-methyl-3-cyclobutene-1,2-dione hydrochloride. (I-1)

26% yield crystallized from MeOH: mp 180°–240° C. (dec); $^1H$ NMR (DMSO, 300 MHz) δ 8.26 (m, 2H), 7.6–7.24 (m, 4 H), 7.10–6.99 (m, 1H), 4.25 (br s, 2H), 3.93 (s, 3 H), 3.57 (br s, 2H), 3.16 (m, 4H), 2.72 (t, J=6.9 Hz, 2H) 2.24 (s, 3H), 2.11 (m, 2H), 1.89 (s, 3H); IR (KBr) n: 3700–2000, 1780, 1725, 1270 $cm^{-1}$; MS (m/e) 459 ($M^+$). Anal. Calcd for $C_{26}H_{29}N_5O_3$·3.89 HCl: C, 51.93; H, 5.51; N, 11.65, Found: C, 51.93; H, 5.70; N, 11.57.

Example 19

3-[[3-[4-(2-Pyridinyl)-1-piperazinyl-]propyl]-1H-indol-5-yl]amino]-4-methyl-3-cyclobutene-1,2-dione hydrochloride. (I-1)

48% yield; mp 175°–185° C. (decomp); $^1H$ NMR (DMSO-$d_6$, 300 MHz) δ 8.11 (d, J=5.3 Hz, 1H), 7.86 (m, 1H), 7.57–6,.88, (m, 6H), 4.45 (d, J=13.9 Hz, 2H), 3.61–3.40 (m, 4H), 3.15–3.08 (m, 2H), 2.73 (t, J=7.0 Hz, 2H), 2.26 (s, 3H), 1.3 $CH_3$), 2.20–2.0 (m, 2H), 1.89 (s, 3H, 1.0 $CH_3$); IR(KBr) 1725, 1785; MS (m/e) 429 ($M^+$).

Example 20

3-[[3-[4-[3-methoxy-2-pyridinyl)-1-piperazinyl] propyl]-1H-indol-5-yl]amino]-4-methyl-3-cyclobutene-1,2-dione hydrochloride. (I-1)

50% yield, crystallized from MeOH; mp 198°–205° C. (dec); $^1H$ NMR (DMSO-$d_6$, 300 MHz) δ 7.81 (d, J=5.1 Hz, 1H), 7.58–7.26 (m, 4H), 7.10–7.01 (m, 2H), 4.05 (d, J=13.3 HZ, 2H), 3.84 (s, 3H), 3.56–3.54 (m, 2H), 3.44–3.331 (m, 2H), 3.18–3.06 (m, 4H), 2.74–2.72 (m, 2H), 2.26 (s, 3H, 1.3 $CH_3$), 2.14–1.99 (m, 2H), 1.90 (s, 3H, 1.0 $CH_3$); IR(KBr) n: 1725, 1785 $cm^{-1}$; MS (m/e) 459 ($M^+$). Anal. Calcd for $C_{26}H_{29}N_5O_3$·HCl(3.5) C, 53.18, H, 5.58, N, 11.93: Found: C, 53.30, H, 5.80, N, 11.93.

Example 21

A compound of Formula I-1 wherein $R^6$ is hydrogen was prepared from the reaction product (6) of Example 6 with 3-(1-methylethoxy)-cyclobut-3-ene-1,2-dione (3).

3-[3-[4-(5-Methoxy-4-pyrimidyl)-1-piperazinyl] propyl]-5-(1,2-dioxo-3-cyclobuten-3-yl)amino-1H-indole (I-1)

52% Yield crystallized from MeOH: mp 125°–130° C.: IR (KBr) 3430, 3185, 1777, 1747, 1582 $cm^{-1}$; $^1H$ NMR (DMSO-$d_6$, 200 MHz) δ 11.26 (br s, 1H), 10.91 (br s, 1H), 8.78 (s, 1H), 8.22 (s, 1H), 8.02 (s, 1H), 7.45 (d, J=1.7 Hz, 1H), 7.37 (d, J=8.7 Hz, 1H), 7.19 (d, J=1.9 Hz, 1H), 7.11 (dd, J=8.6, 1.9 Hz, 1H), 4.10 (q, J=5.2 Hz, 0.7H, MeOH), 3.82 (s, 3H), 3.67 (br s, 4H), 3.16 (d, J=5.1 Hz, 2.1H, MeOH), 2.71 (t, J=7.4 Hz, 2H), 2.50–2.33 (m, 6H), 1.85–1.81 (m, 2H). Anal. Calcd for $C_{24}H_{26}N_6O_3 \cdot H_2O \cdot 0.7\ CH_4O$: C, 60.92; H, 6.37; N, 17.27. Found: C, 60.82; H, 6.00; N, 17.54.

Examples 22 & 23

Examples 22 and 23 were prepared from the reaction of 2-methyl-1-(5-methoxy-4-pyrimidinyl)piperazine (1) and 3-methyl-1-(5-methoxy-4-pyrimidinyl)piperazine (1), respectively, with 5-nitro-3-(3-bromopropyl)indole (Example 4a). Reduction yielded compounds analogous to those of Example 6 which were then reacted with 3-(1-methylethoxy)-cyclobut-3-ene-1,2-dione (3) to afford compounds of Formula I-1 wherein $R^6$ is hydrogen.

Example 22

3-[3-[4-(5-Methoxy-4-pyrimidyl)-3-methyl-1-piperazinyl]propyl]-5-(1,2-dioxo-3-cyclobuten-3-yl)amino-1H-indole (I-1)

36% Yield, crystallized from ethyl acetate: mp 191°–193° C.; IR (KBr) 3420, 1778, 1742, 1575 cm$^{-1}$; $^1$H NMR (CDCl$_3$, 200 MHz) δ 8.35 (s, 1H), 8.32 (s, 1H), 8.11–8.07 (m, 2H), 7.89 (s, 1H), 7.44–7.40 (m, 2H), 7.12 (d, J=2.2 Hz, 1H), 7.03 (dd, J=8.7, 2.2 Hz, 1H), 4.83 (m, 1H), 4.35–4.28 (m, 1H), 3.85 (s, 3H), 3.41–3.29 (m, 1H), 2.91–2.73 (m, 4H), 2.49–2.10 (m, 4H), 1.98–1.87 (m, 2H), 1.33 (d, J=6.7 Hz, 3H). Anal. Calcd for $C_{25}H_{28}N_6O_3 \cdot 0.4\ H_2O \cdot 0.02\ C_4H_8O_2$: C, 64.16 H, 6.22; N, 17.90. Found: C, 64.48; H, 6.16; N, 17.51.

Example 23

3-[3-[4-(5-Methoxy-4-pyrimidyl)-2-methyl-1-piperazinyl]propyl]-5-(1,2-dioxo-3-cyclobuten-3-yl)amino-1H-indole (I-1)

46% Yield on crystallization from isopropanol: mp 195° C. (dec); IR (KBr) 3400, 3200, 1783, 1750, 1600, 1580 cm$^{-1}$; $^1$H NMR (DMSO-d$_6$, 200 MHz) δ 11.40 (br s, 1H), 11.30 (s, 1H), 11.23 (s, 1H), 8.87 (s, 1H), 8.54 (s, 1H), 8.17 (s, 1H), 7.46 (d, J=1.7 Hz, 1H), 7.39 (d, J=8.7 Hz, 1H), 7.28 (d, J=2.0 Hz, 1H), 7.12 (dd, J=8.7, 2.2 Hz, 1H), 4.74 (m, 2H), 3.89 (s, 3H), 3.8–3.0 (m, 8H), 2.79 (m, 2H), 2.06 (m, 2H), 1.36 (d, J=4.9 Hz, 2H), 1.18 (d, J=6.1 Hz, 1H). Anal. Calcd for $C_{25}H_{28}N_6O_3 \cdot 2.5\ HCl$: C, 54.42; H, 5.57; N, 15.24. Found: C, 54.78; H, 5.74; N, 15.15.

Examples 24 & 25 were prepared in a manner similar to Examples 22 & 23 by substituting 3-(1-methylethoxy)-4-methylcyclobut-3-ene-1,2-dione in place of 3-(1-methylethoxy)-4-cyclobut-3-ene-1,2-dione in the final step:

Example 24

3-[3-[4-(5-Methoxy-4-pyrimidyl)-3-methyl-1-piperazinyl]propyl]-5-(1,2-dioxo-4-methyl-3-cyclobuten-3-yl)amino-1H-indole (I-1)

27% Yield on crystallization from acetone: mp 200° C. (dec); IR (KBr) 3400 (br), 3170 (br), 1780, 1727, 1708, 1630, 1598 cm$^{-1}$; $^1$H NMR (DMSO-d$_6$, 200 MHz) d 11.13 (s, 0.5H), 10.99 (s, 0.5H), 10.93 (s, 0.5H), 10.89 (s, 0.5H), 8.64 (s, 1H), 8.21 (s, 1H), 7.57–6.99 (m, 4H), 5.20 (br s, 1H), 4.87 (m, 1H), 3.90 (s, 3H) 3.7–3.4 (m, 3H), 3.11 (br s, 4H), 2.72 (m, 2H), 2.26 (s, 1.6H), 2.14 (m, 2H), 2.08 (s, 4.5H, acetone), 1.90 (s, 1.4H), 1.51 (d, J=6.9 Hz, 3H). Anal. Calcd for $C_{26}H_{30}N_6O_3 \cdot 2\ HCl \cdot 1.2\ H_2O \cdot 0.75\ C_3H_8O$: C, 55.42; H, 6.32; N, 13.73. Found: C, 55.58; H, 6.22; N, 13.43.

Example 25

3-[3-[4-(5-Methoxy-4-pyrimidyl)-2-methyl-1-piperazinyl]propyl]-5-(1,2-dioxo-4-methyl-3-cyclobuten-3-yl)amino-1H-indole (I-1)

36% Yield on crystallization from methanol; mp 212° C. (dec); IR (KBr) 3300, 3270, 1783, 1730, 1598, 1586 cm$^{-1}$; $^1$H NMR (DMSO-d$_6$, 200 MHz) δ 11.06 (s, 0.5H), 10.95 (s, 0.5H), 10.92 (s, 0.5H), 10.76 (s, 0.5H), 10.5 (br s, 1H), 8.31 (s, 1H), 8.13 (s, 1H), 7.57–6.99 (m, 4H), 4.56–4.37 (m, 2H), 3.86 (s, 3H), 3.59–3.16 (m, 7H), 2.74 (br s, 2H), 2.25 (s, 1.6H), 2.04 (br s, 2H), 1.88 (s, 1.4H), 1.30 (d, J=5.2 Hz, 2H), 1.18 (d, J=6.5 Hz, 1H). Anal. Calcd for $C_{26}H_{30}N_6O_3 \cdot HCl \cdot 0.5\ CH_4O$: C, 60.39; H, 6.31; N, 15.95. Found: C, 60.10; H, 6.19; N, 16.01.

Example 26

3-[3-[4-(5-Methoxy-4-pyrimidyl)-1-piperazinyl]propyl]-5-(1,2-dioxo-4-butyl-3-cyclobuten-3-yl)amino-1H-indole (I-1)

This product was prepared in a manner similar to Example 16 by substituting 3-(1-methylethoxy)-4-butylcyclobut-3-ene-1,2-dione in place of 3-(1-methylethoxy)-4-methylcyclobut-3-ene-1,2-dione in the final step:

34% Yield upon trituration with acetone; mp 130° C. (dec); IR (KBr) 3400 (br), 3200 (br), 1778, 1725, 1630, 1597, 1577, 1545 cm$^{-1}$; $^1$H NMR (DMSO-d$_6$, 200 MHz) δ11.06 (s, 0.5H), 10.96 (s, 0.5H), 10.91 (s, 0.5H), 10.67 (s, 1H), 8.54 (s, 1H), 8.18 (s, 1H), 7.56–6.98 (m, 4H), 4.77 (m, 2H), 3.86 (s, 3H), 3.75–3.47 (m, 6H), 3.13 (m, 4H), 2.71 (m, 2H), 2.26 (m, 1H), 2.07 (m, 2H), 1.65 (m, 1H), 1.38 (m, 1H), 0.92 (m, 3H), 0.56 (m, 1H). Anal. Calcd for $C_{28}H_{34}N_6O_3 \cdot 2.2\ HCl \cdot H_2O \cdot 0.1\ C_3H_6O$: C, 56.03; H, 6.45; N, 13.85. Found: C, 56.21; H, 6.46; N, 13.56.

2. Formula I-2 Compounds

Example 27

3-[3-[4-(5-Methoxy-4-pyrimidyl)-1-piperazinyl]propyl]-5-(1,2-dioxo-3-cyclobuten-3-yl)methylamino-1H-indole (I-1)

To a solution of 3-[3-[4-(5-methoxy-4-pyrimidyl)-1-piperazinyl]propyl]-5-(1,2-dioxo-3-cyclobuten-3-yl)aminoindole (I-1) (0.410 g, 0.92 mmol) in 110 mL of dry THF was added dropwise a solution of n-BuLi (1.6M in hexane, 0.633 mL, 1.01 mmol), at –78° C. under Ar. The mixture was kept at –78° C. for 2 h and then at 0° C. for 1 h. To the resulting suspension was added iodomethane (0.135 mL, 2.10 mmol) and stirring was continued at 0° C. for 1 h and then the mixture was allowed to warm to room temperature overnight. The reaction mixture was then diluted with ethyl acetate, washed (H$_2$O, brine), dried (Na$_2$SO$_4$) and evaporated to give an orange foam. Flash chromatography (SiO$_2$/CH$_2$Cl$_2$ then CH$_2$Cl$_2$—MeOH, 95:5 and finally CH$_2$Cl$_2$—MeOH—NH$_4$OH, 95:4.7:0.3) afforded the title compound (0.140 g, 33%) as an orange foam. This material was taken up in excess methanolic HCl, the solution was evaporated and the residue triturated with isopropanol to give a solid. Crystallization from methanol-acetone gave the hydrochloride (0.100 g, 20%) as an off-white solid, mp 170° C. (dec):

IR (KBr) 3420, 1775, 1740, 1600 cm$^{-1}$; $^1$H NMR (DMSO-d$_6$, 200 MHz) δ 11.45 (br s, 0.5H), 11.83–11.81 (br d, 0.7H), 8.60 (s, 1H), 8.51 (s, 0.4H), 8.19 (s, 1H), 8.11 (s, 0.6H), 7.66–7.58 (m, 1H), 7.46–7.30 (m, 2H), 7.19–7.08 (m, 1H), 4.89–4.82 (m, 2H), 3.90 (s, 3H), 3.74 (s, 1.6H), 3.55 (s, 1.4H), 3.8–3.4 (m, 4H), 3.11 (m, 4H), 2.77 (m, 2H), 2.10 (m, 2H). Anal. Calcd for C$_{25}$H$_{28}$N$_6$O$_3$. 2.5 HCl: C, 54.42; H, 5.57; N, 15.24. Found: C,54.21; H, 5.82; N, 15.08.

3. Formula I-3 Compounds

Example 28

The compound of Example 6 was reacted with 3,4-bis(1-methylethoxy)cyclobut-3-ene-1,2-dione (2) to provide Example 29:

3-[3-[4-(5-Methoxy-4-pyrimidyl)-1-piperazinyl]propyl]-5-[1,2-dioxo-4-(1-methylethoxy)-3-cyclobuten-3-yl]amino-1H-indole (I-3)

A solution of 3-[3-[4-(5-methoxy-4-pyrimidyl)-1-piperazinyl]propyl]-5-aminoindole (6) (0.208 g, 0.56 mmol) and 3,4-bis (1-methylethoxy) cyclobut-3-ene-1,2-dione[4] (2) (0.112 g, 0.56 mmol) in 5 mL of absolute ethanol was stirred at room temperature for 66 h and then it was heated at ca. 80° C. (oil-bath temperature) for 4 h. The cooled mixture was filtered and the residue was washed with ethanol and then dried in vacuo to give the title compound (0.190 g, 64%) as a slightly pinkish solid, mp 140°–143° C.: IR (KBr) 3312, 1800, 1720, 1607, 1588 cm$^{-1}$; $^1$H NMR (DMSO-d$_6$, 200 MHz) δ 10.80 (s, 1H), 10.7 (br s, 1H), 8.22 (s, 1H), 8.01 (s, 1H), 7.48 (m, 1H), 7.28 (d, J=8.6 Hz, 1H), 7.14 (s, 1H), 7.06 (m, 1H), 5.40 (m, 1H), 3.81 (s, 3H), 3.65 (br s, 4H), 3.42 (q, J=7.0 Hz, 0.6H, CH$_3$CH$_2$OH), 2.67 (m, 2H), 2.43 (m, 4H), 2.35 (m, 2H), 1.82 (m, 2H), 1.41 (d, J=6.1 Hz, 6H), 1.04 (t, J=7.0 Hz, 0.9H, CH$_3$CH$_2$OH). Anal. Calcd for C$_{27}$H$_{32}$N$_6$O$_4$. 0.5 H$_2$O. 0.3 C$_2$H$_6$O: C, 62.85; H, 6.65; N, 15.94. Found: C, 62.85; H, 6.46; N, 16.17.

[4.] Cf: Example 9.

Example 29

Example 30 is prepared by hydrolysis of the compound of Example 29:

3-[3-[4-(5-Methoxy-4-pyrimidyl)-1-piperazinyl]propyl]-5-(1,2-dioxo-4-hydroxy-3-cyclobuten-3-yl)amino-1H-indole (I-1)

To a solution of 3-[3-[4-(5-methoxy-4-pyrimidyl)-1-piperazinyl]propyl]-5 [1,2-dioxo-4-(1-methylethoxy)-3-cyclobuten-3-yl]aminoindole (I-3) (0.175 g, 0.35 mmol) in 5 mL of methanol was added 0.10 mL (0.60 mmol) of 6N HCl and the mixture was heated at ca. 80° C. for 5 h. Another 0.10 mL (0.60 mmol) of 6N HCl was then added, as well as 0.20 mL of H$_2$O, and the mixture was heated at ca. 100° C. for 18 h. On cooling to room temperature, the resulting suspension was filtered and the residue was washed (acetone, ether) and then air-dried. This solid (0.130 g) was taken up in methanol and the resulting solution was treated with charcoal, filtered and evaporated to give the hydrochloride salt of the title compound (0.075 g, 36%) as a beige solid, mp 215° C. (dec): IR (KBr) 3410 (br), 3240 (br), 1783, 1700, 1632, 1547 cm$^{-1}$; $^1$H NMR (DMSO-d$_6$, 200 MHz) δ10.88 (s, 1H), 10.37 (s, 1H), 8.56 (s, 1H), 8.19 (s, 1H), 7.62 (s, 1H), 7.29 (d, J=8.6 Hz, 1H), 7.21 (s, 1H), 7.10 (dd, J=8.6, 1.8 Hz, 1H), 4.80 (br m, 2H), 3.90 (s, 3H), 3.57 (br m, 4H), 3.13 (br m, 4H), 2.73 (m, 2H), 2.12 (m, 2H). Anal. Calcd for C$_{24}$H$_{26}$N$_6$O$_4$. 3 HCl. H$_2$O: C, 48.86; H, 5.30; N, 14.25. Found: C, 48.81; H, 5.51; N, 14.22.

4. Formula I-4 Compounds

Example 30

3-[3-[4-(5-Methoxy-4-pyrimidyl)-1-piperazinyl]propyl]-5-(1,2-dioxo-4-methylamino-3-cyclobuten-3-yl)amino-1H-indole (I-4)

Into 10 mL of absolute ethanol cooled at 5° C. was bubbled methylamine for 10 min. To this solution was added a solution of 3-[3-[4-(5-methoxy-4-pyrimidyl)-1-piperazinyl]propyl]-5-[1,2-dioxo-4-(1-methylethoxy)-3-cyclobuten-3-yl]aminoindole (I-3) (0.30 g, 0.59 mmol) in 5 mL of dichloromethane and the mixture was stirred at 5° C. for 30 min. The resulting suspension was filtered and the residue was dried to give 0.20 g of the title compound as a white solid. Evaporation of the filtrate gave an additional 0.04 g of solid material. Total yield=0.24 g (86%). The solid was taken up in excess methanolic HCl with gentle warming and the resulting solution was stored at 5° C. to give a solid. The mixture was diluted with ether and then it was filtered and the residue was dried in vacuo to give the hydrochloride (0.23 g, 67%) as a light yellow solid, mp 115°"120° C.: IR (KBr) 3420 (br), 3240 (br), 1792, 1665, 1632, 1608, 1547 cm$^{-1}$; $^1$H NMR (DMSO-d$_6$ , 200 MHz) δ 11.07 (br s, 1H), 10.84 (d, J=1.7 Hz, 1H), 10.59 (br s, 1H), 8.67 (s, 1H), 8.43 (br s, 1H), 8.20 (s, 1H), 7.75 (s, 1H), 7.28 (d, J=8.6 Hz, 1H), 7.18 (d, J=2.2 Hz, 1H), 7.14 (dd, J=8.7, 1.9 Hz, 1H), 4.93 (m, 2H), 3.91 (s, 3H), 3.62 (m, 4H), 3.21 (d, J=4.9 Hz, 3H), 3.2–3.0 (m, 4H), 2.73 (t, J=6.8 Hz, 2H), 2.12 (m, 2H). Anal. Calcd for C$_{25}$H$_{29}$N$_7$O$_3$. 3 HCl: C, 51.33; H, 5.52; N, 16.76. Found: C, 51.57; H, 5.58; N, 16.74.

Example 31

3-[3-[4-(5-Methoxy-4-pyrimidyl)-1-piperazinyl]propyl]-5-(1,2-dioxo-4-amino-3-cyclobuten-3-yl)amino-1H-indole (I-4)

Into 25 mL of absolute ethanol cooled at 0° C. was bubbled anhydrous ammonia for 20 min. To this solution was added a solution of 3-[3-[4-(5-methoxy-4-pyrimidyl)-1-piperazinyl]propyl]-5-[1,2-dioxo-4-(1-methylethoxy)-3-cyclobuten-3-yl]aminoindole (I-3) (0.300 g, 0.59 mmol) in 10 mL of dichloromethane and the mixture was stirred at 0° C. for 1 h. The reaction mixture was then transferred to a bomb and heated to ca. 40° C. for 1 h. After being stirred at room temperature for an additional 18 h, the mixture was filtered and the residue was washed with dichloromethane and then dried in vacuo to give the title compound (0,198 g, 77%) as a grayish solid. The solid was taken up in excess methanolic HCl and on standing at room temperature a solid was deposited. This material was filtered, washed (acetone, ether) and then dried in vacuo to give the hydrochloride (0.220 g, 73%) as a light yellow solid, mp 200° C. (dec): IR (KBr) 3200 (br), 1796, 1675, 1633, 1577, 1550, 1442 cm$^{-1}$; $^1$H NMR (DMSO-d$_6$, 200 MHz) δ 10.81 (br s, 2H), 10.49 (br s, 1H), 8.60 (s, 1H), 8.17 (m, 2H), 7.73 (s, 1H), 7.30–7.16 (m, 3H), 4.86 (m, 2H), 3.89 (s, 3H), 3.58 (br s, 4H), 3.12 (br s, 4H), 2.72 (br s, 2H), 2.12 (br s, 2H). Anal. Calcd for C$_{24}$H$_{27}$N$_7$O$_3$. 2 HCl. 0.55 H$_2$O: C, 52.95; H, 5.57; N, 18.02. Found: C, 52.93; H, 5.53; N, 17.86.

Example 32

3-[3-[4-(5-Methoxy-4-pyrimidyl)-1-piperazinyl] propyl]-5-(1,2-dioxo-4-dimethylamino-3-cyclobuten-3-yl)amino-1H-indole (I-4)

Into 25 mL of absolute ethanol cooled at 0° C. was bubbled dimethylamine for 10 min. To this solution was added a solution of 3-[3-[4-(5-methoxy-4-pyrimidyl)-1-piperazinyl]propyl]-5[1,2-dioxo-4-(1-methylethoxy)-3-cyclobuten-3-yl]aminoindole(I-3) (0,290 g, 0.57 mmol) in 5 mL of dichloromethane and then the mixture was stirred at room temperature for 18 h. The resulting solution was evaporated to give a gum which was chromatographed ($SiO_2/CH_2Cl_2$—MeOH, 95: 5 then $CH_2Cl_2$—MeOH-$NH_4OH$, 95:4.5:0.5 to 90:9:1) to give a solid which was triturated with methanol-isopropanol to give the title compound (0.120 g, 43%) as a white solid, mp 150° C. (dec): IR (KBr) 3280, 1790, 1662, 1580 $cm^{-1}$; $^1H$ NMR (DMSO-$d_6$, 200 MHz) δ 10.74 (s, 1H), 9.40 (s, 1H), 8.23 (S, 1H), 8.02 (s, 1H), 7.34 (s, 1H), 7.26 (d, J=8.6 Hz, 1H), 7.12 (s, 1H), 7.00 (d, J=8.6 Hz, 1H), 3.82 (s, 3H), 3.66 (br s, 4H), 3.30 (s, 3H), 3.22 (s, 3H), 2.66 (m, 2H), 2.6–2.4 (m, 4H), 2.34 (m, 2H), 1.81 (m, 2H). Anal. Calcd for $C_{26}H_{31}N_7O_3$. 0.7 $H_2O$: C, 62.18; H, 6.50; N, 19.53. Found: C, 62.00; H, 6.38; N, 19.52.

5. Formula I-5 Compounds

These products are readily prepared by alkylation of appropriate compounds of Formula I-4 with, generally, an alkyl halide, an acyl halide, or an alkylsulfonyl halide to give the desired I-5 product.

C. Indolyl-Squarates

1. Formula I-6 Compounds

Example 33

3-[3-[4-(5-Methoxy-4-pyrimidinyl)-1-piperazinyl)propyl]-5-(1,2-dioxo-4-methylamino-3-cyclobuten-3-yl)indole (I-6)

A. 3-[3-[4-(5-Methoxy-4-pyrimidyl)-1-piperazinyl]propyl]-5-(1,2-dioxo-4-methylamino-3-cyclobuten-3-yl)-1-triisopropylsilyl-1H-indole A mixture of 5-(1,2-dioxo-4-methylamino-3-cyclobuten-3-yl)-3-[3-(p-toluenesulfonyl)oxypropyl]-1-triisopropylsilylindole (14) 0.247 g, 0.42 mmol), 1-(5-methoxy-4-pyrimidyl)piperazine (1) (0.081 g, 0.42 mmol), finely pulverized KI (0.070 g, 0.42 mmol) and diisopropylethylamine (0.37 mL, 2.1 mmol) in 10 mL of acetonitrile was heated to reflux under Ar for 18 h. The cooled reaction mixture was diluted with ethyl acetate and washed with water. The aqueous phase was back-extracted with dichloromethane (2x) and the combined organic phase was dried ($Na_2SO_4$) and evaporated to give a yellow foam. The foam was chromatographed ($SiO_2$/ethyl acetate—MeOH—$NH_4OH$, 90:9:1 then MeCN—MeOH—$NH_4OH$, 90:9:1) to give the title compound (0.207 g, 80%) as a yellow foam: IR (neat) 3280 (br), 1770, 1720, 1595 (br), 1140 $cm^{-1}$; $^1H$ NMR (CDCl$_3$, 200 MHz) δ 8.34 (s, 1H), 8.08 (d, J=1.5 Hz, 1H), 7.92 (s, 1H), 7.75 (m, 1H), 7.54 (d, J=8.7 Hz, 1H), 7.06 (s, 1H), 6.8 (br s, 1H), 3.90 (br s, 2H), 3.86 (s, 3H), 3.51 (d, J=4.9 Hz, 2H), 3.41 (d, J=4.9 Hz, 2H), 3.2–2.8 (m, 4H), 2.8–2.6 (m, 4H), 2.4–2.0 (m, 4H), 1.67 (hept, J=7.5 Hz, 3H), 1.13 (d, J=7.5 Hz, 18H).

B. 3-[3-[4-(5-Methoxy-4-pyrimidyl)-1-piperazinyl]propyl]-5-(1,2-dioxo-4-methylamino-3-cyclobuten-3-yl)-1H-indole (I-6)

To an ice-cold solution of 3-[3-[4-(5-methoxy-4-pyrimidyl)-1-piperazinyl]propyl]-5 (1,2-dioxo-4-methylamino-3-cyclobuten-3-yl)-1-triisopropyl-silylindole (0.196 g, 0.32 mmol) in 5 mL of THF was added dropwise a solution of tetrabutylammonium fluoride (TBAF) (1M in THF, 0.32 mL, 0.32 mmol) and the mixture was stirred for 1 h. The reaction was then quenched with saturated aqueous $NH_4Cl$, diluted with water and extracted with ethyl acetate (2x) and then dichloromethane. The combined organic extracts were washed (brine), dried ($Na_2SO_4$) and evaporated. Flash chromatography ($SiO_2$/ethyl acetate—MeOH—$NH_4OH$, 90:9:1) of the residue gave the title compound (0.054 g, 37%) as a light yellow solid. This material was triturated with methanol and the residue was filtered, washed (methanol, ether) and dried in vacuo to give the analytical sample as a cream-coloured solid (25%), mp 225°–228° C. (dec): IR (KBr) 3310, 1768, 1698, 1582 $cm^{-1}$; $^1H$ NMR (DMSO-$d_6$, 400 MHz) d 11.14 (s, 1H), 8.84 (q, J=4.8 Hz, 1H), 8.22 (s, 2H), 8.01 (s, 1H), 7.78 (dd, J=8.5, 1.5 Hz, 1H), 7.45 (d, J=8.5 Hz, 1H), 7.24 (d, J=1.9 Hz, 1H), 3.82 (s, 3H), 3.67 (br s, 4H), 3.34 (d, J= 4.8 Hz, 3H), 2.77 (t, J=7.5 Hz, 2H), 2.45 (br s, 4H), 2.38 (t, J=7.1 Hz, 2H), 1.86 (m, 2H). Anal. Calcd for $C_{25}H_{28}N_6O_3$. 0.4 $H_2O$: C, 64.20; H, 6.21; N, 17.97. Found: C, 64.13; H, 6.01; N, 17.81.

Examples 35–37 were prepared in a manner similar to Example 34.

Example 34

3-[3-[4-(5-Methoxy-4-pyrimidinyl)-1-piperazinyl] propyl]-5-(1,2-dioxo-4-amino-3-cyclobuten-3-yl)-1H-indole (I-6)

A. 3-[3-[4-(5-Methoxy-4-pyrimidyl)-1-piperazinyl]propyl]-5-(1,2-dioxo-4-amino-3-oyclobuten-3-yl)-1-triisopropylsilyl-1H-indole IR (neat) 3330 (br), 3180 (br), 1775, 1725, 1660, 1580, 1410 $cm^{-1}$; $^1H$ NMR (CDCl$_3$, 200 MHz) δ 8.34 (s, 1H), 8.17 (s, 1H), 7.93 (s, 1H), 7.84 (m, 1H), 7.56 (d, J=8.7 Hz, 1H), 7.07 (s, 1H), 6.87 (br s, 1H), 5.41 (br s, 1H), 3.95 (br s, 4H), 3.86 (s, 3H), 2.95–2.67 (m, 8H), 2.12 (m, 2H), 1.68 (hept, J=7.5 Hz, 3H), 1.13 (d, J=7.4 Hz, 18H).

B. 3-[3-[4-(5-Methoxy-4-pyrimidyl)-1-piperazinyl]propyl]-5-(1,2-dioxo-4-amino-3-cyclobuten-3-yl)-1H-indole (I-6)

To a solution of 3-[3-[4-(5-methoxy-4-pyrimidyl)-1-piperazinyl]propyl]-5-(1,2-dioxo-4-amino-3-cyclobuten-3-yl)-1-triisopropylsilylindole (0.280 g, 0.465 mmol) in 10 mL of acetonitrile was added 48% HF (34 μL, 0.94 mmol) and the mixture was stirred at room temperature for 2 h. The resulting suspension was filtered and the residue was washed with acetonitrile and ether, and then it was air-dried to give a pale yellow solid. The solid was suspended in saturated aqueous $NaHCO_3$ with vigorous stirring and the suspension was then filtered and the residue was washed with water, a little ethanol and finally with ether. This material was dried in vacuo to give the title compound (0.194 g, 94%) as a yellow solid. Crystallization from ethanol afforded the analytical sample (0.141 g, 68%) as a beige solid, mp 233° C. (dec): IR (KBr) 3330, 3195, 1772, 1700, 1660, 1577 $cm^{-1}$; $^1H$ NMR (DMSO-$d_6$, 200 MHz) d 11.15 (br s, 1H), 8.93 (br s, 1H), 8.83 (br s, 1H), 8.27 (s, 1H), 8.22 (s, 1H), 8.01 (s, 1H), 7.83 (d, J=8.5 Hz, 1H), 7.44 (d, J=8.5 Hz, 1H), 7.24 (s, 1H), 3.81 (s, 3H), 3.67 (br s, 4H), 2.81–2.73 (m, 2H), 2.49–2.35 (m, 6H), 1.88–1.81 (m, 2H). Anal. Calcd for $C_{24}H_{26}N_6O_3$. 0.5 $H_2O$. 0.25 $C_2H_6O$: C, 63.06; H, 6.12; N, 18.08. Found: C, 63.32; H, 5.83; N, 17.73.

Example 35

3-[3-[4-(5-Methoxy-4-pyrimidinyl)-1-piperazinyl] propyl]-5-(1,2-dioxo-4-isopropylamino-3-cyclobuten-3-yl)-1H-indole (I-6)

A. 3-[3-[4-(5-Methoxy-4-pyrimidyl)-1-piperazinyl]propyl]-5-(1,2-dioxo-4-isopropylamino-3-cyclobuten-3-yl)-1-triisopropylsilyl-1H-indole IR (neat) 3280 (br), 1769, 1719, 1580, 1410 cm$^{-1}$; $^1$H NMR (CDCl$_3$, 200 MHz) δ 8.34 (s, 1H), 8.24 (s, 1H), 7.93 (s, 1H), 7.75 (br m, 1H), 7.55 (d, J=8.6 Hz, 1H), 7.07 (s, 1H), 4.76 (br m, 1H), 3.98 (br s, 4H), 3.87 (s, 3H), 2.95 (m, 2H), 2.8–2.6 (m, 6H), 2.48 (m, 2H), 1.68 (hept, J=7.5 Hz, 3H), 1.43 (d, J=6.5 Hz, 6H), 1.13 (d, J=7.5 Hz, 18H).

B. 3-[3-[4-(5-Methoxy-4-pyrimidyl)-1-piperazinyl]propyl]-5-(1,2-dioxo-4-isopropylamino-3-cyclobuten-3-yl)-1H-indole (I-6)

To a solution of 3-[3-[4-(5-methoxy-4-pyrimidyl)-1-piperazinyl]propyl]-5-(1,2-dioxo-4-isopropylamino-3-cyclobuten-3-yl) -1-triisopropylsilylindole (0.270 g, 0.42 mmol) in 10 mL of acetonitrile was added 48% HF (30 µL, 0.84 mmol) and the mixture was stirred at room temperature for 2 h. The resulting mixture was evaporated and the residue was partitioned between saturated aqueous NaHCO$_3$ and ethyl acetate. The organic phase was separated and the aqueous phase was back-extracted with ethyl acetate. The combined organic extracts were dried (Na$_2$SO$_4$) and evaporated to give a yellow foam. Crystallization from ethanol at –20° C. afforded the title compound (0.192 g, 94%) as a light yellow solid, mp 104°–106° C.: IR (KBr) 3230 (br), 1768, 1710, 1580 (br) cm$^{-1}$; $^1$H NMR (DMSO-d$_6$, 200 MHz) δ11.15 (s, 1H), 8.77 (d, J=8.6 Hz, 1H), 8.35 (s, 1H), 8.22 (s, 1H), 8.01 (s, 1H), 7.75 (d, J=8.5 Hz, 1H), 7.46 (d, J=8.5 Hz, 1H), 7.25 (d, J=1.7 Hz, 1H), 4.59 (m, 1H), 4.35 (t, J=5.1 Hz, 2H), 3.82 (s, 3H), 3.68 (br s, 4H), 3.43 (m, 1.7H, CH$_3$C H$_2$OH), 2.78 (t, J=7.4 Hz, 2H), 2.5–2.3 (m, 6H), 1.86 (m, 2H), 1.31 (d, J=6.5 Hz, 6H), 1.05 (t, J=7.0 Hz, 2.6H, C H$_3$CH$_2$OH). Anal. Calcd for C$_{24}$H$_{26}$N$_6$O$_3$. 0.5 H$_2$O. 0.85 C$_2$H$_6$O: C, 64.22; H, 7.15; N, 15.66. Found: H, 6.78; N, 15.48.

Example 36

3-[3-[4-(5-Methoxy-4-pyrimidyl)-1-piperazinyl] propyl-5-(1,2-dioxo-4-t-butylamino-3-cyclobuten-3-yl)-1H-indole (I-6)

A. 3-[3-[4-(5-Methoxy-4-pyrimidyl)-1-piperazinyl]propyl]-5-(1,2-dioxo-4-t-butylamino-3-cyclobuten-3-yl)-1-triisopropylsilyl-1H-indole IR (neat) 3300, 1766, 1717, 1582, 1565 cm$^{-1}$; $^1$H NMR (CDCl$_{13}$, 200 MHz) δ 8.29 (s, 1H), 8.24 (d, J=1.5 Hz, 1H), 7.84 (s, 1H), 7.54 (d, J=8.6 Hz, 1H), 7.42 (dd, J=8.7, 1.6 Hz, 1H), 7.05 (s, 1H), 6.32 (s, 1H), 3.81 (S, 3H), 3.76 (m, 4H), 2.80 (t, J=7.4 Hz, 2H), 2.52 (m, 4H), 2.44 (m, 2H), 1.92 (m, 2H), 1.65 (hept, J=7.5 Hz, 3H), 1.55 (s, 9H), 1.10 (d, J=7.5 Hz, 18H).

B. 3-[3-[4-(5-Methoxy-4-pyrimidyl)-1-piperazinyl]propyl]-5-(1,2-dioxo-4-t-butylamino-3-cyclobuten-3-yl)-1H-indole (I-6)

To a solution of 3-[3-[4-(5-methoxy-4-pyrimidyl)-1-piperazinyl]propyl]-5-(1,2-dioxo-4-t-butylamino-3-cyclobuten-3-yl)-1-triisopropylsilylindole (0.294 g, 0.45 mmol) in 10 mL of acetonitrile was added 48% HF (32 µL, 0.90 mmol) and the mixture was stirred at room temperature for 2 h. The resulting mixture was evaporated and the residue was partitioned between saturated aqueous NaHCO$_3$ and ethyl acetate. The organic phase was separated and the aqueous phase was back-extracted with ethyl acetate. The combined organic extracts were dried (Na$_2$SO$_4$) and evaporated to give the title compound (0.213 g, 94%) as a yellow foam which could not be crystallized. This material was suspended in excess 1N HCl, a small amount of ethanol was added and the mixture was gently warmed to effect dissolution. Storage of this solution at –20° C. led to crystallization. The crystals were filtered, washed (acetone, ether) and dried in vacuo to give the hydrochloride (0.252 g, 89%) as a light yellow solid, mp 180° C. (softens), 215°–218° C. (foams): IR (KBr) 3400 (br), 1775, 1715, 1635, 1575 (br) cm$^{-1}$; $^1$H NMR (DMSO-d$_6$, 200 MHz) δ 11.58 (br s, 1H), 11.32 (br s, 1H), 8.67 (s, 1H), 8.46 (s, 1H), 8.32 (s, 1H), 8.21 (s, 1H), 7.84 (d, J=8.6 Hz, 1H), 7.49 (d, J=8.4 Hz, 1H), 7.33 (s, 1H), 4.93 (m, 2H), 3.91 (s, 3H), 3.79–3.62 (m, 4H), 3.17 (br s, 4H), 2.84 (t, J=7.0 Hz, 2H), 2.17 (m, 2H), 1.51 (s, 9H). Anal. Calcd for C$_{28}$H$_{34}$N$_6$O$_3$. 3 HCl. H$_2$O: C, 53.38; H, 6.24; N, 13.34. Found: C, 53.24; H, 6.35; N, 13.24.

Example 37

Agonist Studies in the Canine Lateral Saphenous Vein

The lateral saphenous vein is obtained from an anesthetized dog and trimmed of adherent material. The vessel is then cut into 2–3 mm ring segments and mounted between stainless steel wires in tissue baths containing 20 mL of modified Kreb's buffer which is continuously aerated with 5% CO$_2$/95%O$_2$ and maintained at 37° C. Resting tension is manually adjusted to 1 gram and maintained until a stable baseline is achieved for an equilibration period of 1 h. Tissue bath solution is replaced every 15 min during this equilibration.

Ketanserin, atropine and pyrilamine are added to the baths at a concentration of 1 µM to block 5-HT$_2$, cholinergic and histaminic effects. After 15 min, with the antagonists in place, a serotonin concentration response curve is conducted in a cumulative fashion. At the conclusion the baths are washed out several times, tension is readjusted to 1 gram and the tissue is allowed to return to equilibrium over a period of 45–60 min. The antagonists are again added to the baths and after 15 min, concentration response curves are generated for selected test compounds. Individual vessel segments are only exposed to one test compound.

The activity of test compounds is expressed in terms of relative potency and efficacy compared with 5-HT (arbitrarily assigned a value of 1.0) in the same vascular preparation.

Further Detailed Description

Additional experimental description is given here in order to provide guidance to variation of the R$^1$ moiety which is located at the 4-position of the indole ring system.

Example 40

3-[3-[4-(5-Methoxy-4-primidinyl)-1-piperazinyl] propyl]-5-(1,2-dioxo-4-methyl-3-cyclobuten-3-yl)aminoindole A. 4-Methylindole A mixture of 3-nitro-o-xylene (13.4 mL, 0.1 mol), dimethylformamide dimethyl acetal (40 mL, 0.3 mol) and pyrrolidine (10 mL, 0.12 mol) in 200 mL of dry DMF was heated at 120°–130° C. (oil-bath temperature) under Ar for 21 h. The cooled mixture was poured into cold water (400 mL) and extracted with ether (4×200 mL). The ethereal solution was washed (H$_2$O, 4×100 mL), dried (Na$_2$SO$_4$) and evaporated to give a dark red viscous oil. This oil was taken up in 150 mL of ethyl acetate, 1.5 g of 10% palladium-on-charcoal was added and the mixture was hydrogenated at 50 psi on a Parr shaker for 1 h. The reaction mixture was then filtered, the catalyst was washed with additional ethyl acetate and the filtrate was evaporated to give a dark purple oil. Flash chromatography (SiO$_2$/dichloromethane-petroleum ether, 1:1) of this oil gave pure 4-methylindole (8.85 g, 68%) as a light yellow-brown oil: $^1$H NMR (DMSO-d$_6$, 200 MHz) δ 11.04 (br s, 1H), 7.29(t, J=2.7 Hz, 1H), 7.21 (d, J=7.7 Hz, 1H), 6.96 (t, J=7.2 Hz, 1H), 6.75 (dt, J=6.9, 0.8 Hz, 1H), 6.43 (m, 1H), 2.46 (s, 3H).

B. 1-Acetyl-4-methylindoline

To a solution of 4-methylindole (7.433 g, 0.0567 mol) in 100 mL of glacial acetic acid was added NaCNBH$_3$ (7.25 g, 0.12 mol) portionwise over 1.5 h. The reaction mixture was then concentrated in vacuo, water was added and the solution was basified with 10N NaOH. The resulting mixture was extracted with ethyl acetate (×3) and the organic extract was washed (brine), dried (Na$_2$SO$_4$) and evaporated to give an oil. Flash chromatography (SiO$_2$/ethyl acetate-hexane, 1:4) of this oil gave pure 4-methylindoline (6.962 g, 92%) as an oil: $^1$H NMR (DMSO-d$_6$, 200 MHz) δ 6.78 (t, J=7.6 Hz, 1H), 6.33 (d, J=7.4 Hz, 1H), 6.30 (d, J=7.6 Hz, 1H), 5.36 (br s, 1H), 3.38 (t, J=8.5 Hz, 2H), 2.81 (t, J=8.5 Hz, 2H), 2.11 (s, 3H).

The resulting oil (6.945 g, 0.0522 mol) was taken up in 10 mL of acetic anhydride. An exothermic reaction ensued and after 15 min the mixture had solidified. The volatiles were subsequently removed in vacuo to give a solid. Trituration of this material with ether afforded 6.317 g of 1-acetyl-4-methylindoline as a white crystalline solid, mp 110°–111° C. Evaporation of the supernatant and trituration of the resulting residue with hexane gave an additional 2.191 g of the pure product. Total yield =8.508 g (93%): IR (neat) 1649 cm$^{-1}$: $^1$H NMR (DMSO-d$_6$, 200 MHz) δ 7 86 (d, J=7.9 Hz, 1H), 7.03 (t, J=7.7 Hz, 1H), 6.80 (d, J=7.5 Hz, 1H), 4.08 (t, J=8.5 Hz, 2H), 3.03 (t, J=8.5 Hz, 2H), 2.18 (s, 3H), 2.13 (s, 3H). Anal. Calcd for C$_{11}$H$_{13}$NO: C, 75.39; H, 7.48; N, 8.00. Found: C, 75.41; H, 7.53; N, 7.95.

C. 4-Methyl-5-nitroindoline

A solution of 1-acetyl-4-methylindoline (8.260 g, 0.0372 mol) in 50 mL of concentrated H$_2$SO$_4$ was cooled at 5° C. and then HNO$_3$ was added dropwise so as to maintain an internal temperature of 5°–10° C. After the addition was completed the mixture was kept at the same temperature for 15 min and then it was poured into 500 mL of crushed ice and the resulting slurry was stirred until all the ice had melted. The suspension was then filtered, the filter-cake was washed with water and the residue was taken up in dichloromethane. The organic phase was separated and the aqueous phase was reextracted with dichloromethane (×3). The combined organic phase was dried (Na$_2$SO$_4$) and evaporated to give a dark yellow solid. Chromatography (9×10 cm SiO$_2$ pad/dichloromethane then dichloromethane-acetonitrile, 95:5) of this solid gave an inseparable mixture of 1-acetyl-4-methyl-5-nitroindoline and 1-acetyl-4-methyl-7-nitroindoline (8.090 g, 78%), in a ratio of ca. 9:1: $^1$H NMR (DMSO-d$_6$, 200 MHz) δ 7.98 (d, J=8.9 Hz, 0.88H), 7.89 (d, J=8.9 Hz, 0.88H), 7.54 (d, J=8.3 Hz, 0.12H), 7.03 (d, J=8.3 Hz, 0.12H), 4.18 (t, J=8.7 Hz, 2H), 3.14 (t, J=8.7 Hz, 2H), 2.37 (s, 3H), 2.19 (s, 3H).

To a suspension of 1-acetyl-4-methyl-5(7)-nitroindoline (8.049 g, 0.0366 mol) in 75 mL of methanol was added 25 mL of Claisen's alkali (c.f. Rieser & Fieser, Reagents for Organic Synthesis, Vol. 1, pg. 153) and the resulting mixture was warmed on a steam bath until it became homogeneous. The cooled reaction mixture was concentrated and then it was diluted with water and the resulting suspension was filtered to give an orange-brown solid. The filtrate was extracted with dichloromethane (×3) and the organic extract was dried (Na$_2$SO$_4$) and evaporated to give a solid. The combined solids were chromatographed (SiO$_2$/ether-hexane, 1:1 then chloroform)) to give two fractions. Fraction 1 was taken up in ether and the solution was treated with decolourizing charcoal, filtered (Celite) and evaporated to give 4-methyl-7-nitroindoline (0.575 g, 9%) as a dark orange solid, mp 125°–127° C.; IR (KBr) 3395, 1623, 1596 cm$_{-1}$; $^1$H NMR (DMSO-d$_6$, 200 MHz) δ 7.83 (br s, 1H), 7.55 (d, J=8.8 Hz, 1H), 6.36 (d, J=8.8 Hz, 1H), 3.75 (t, J=8.6 Hz, 1H), 2.99 (t, J=8.6 Hz, 2H), 2.15 (s, 3H). Anal. Calcd for C$_9$H$_{10}$N$_2$O$_2$: C, 60.66; H, 5.66; N, 15.72. Found: C, 60.99; H, 5.71 N, 15.48. Fraction 2 was rechromatographed (chloroform) to give a solid which was triturated with ether to give 4-methyl-5-nitroindoline (4.813 g, 74%) as an orange crystalline solid, mp 169°–171° C.: IR (KBr) 3330, 1598 cm$^{-1}$; $^1$H NMR (DMSO-d$_6$, 200 MHz) δ 7.85 (d, J=8.8 Hz, 1H), 7.04 (br s, 1H), 6.33 (d, J=8.8 Hz, 1H), 3.63 (t, J=8.8 Hz, 1H), 2.98 (t, J=8.8 Hz, 2H), 2.38 (s, 3H) Anal. Calcd for C$_9$H$_{10}$N$_2$O$_2$: C, 60.66; H, 5.66; N, 15.72. Found: C, 60.66; H, 5.47; N, 15.74.

D. 4-Methyl-5-nitroindole

To a suspension of 4-methyl-5-nitroindoline (4.767 g, 0.0268 mol) in 100 mL of methanol was added 2,3-dichloro-5,6-dicyano-1,4-benzoquinone (6.697 g, 0.0295 at room temperature for 1 h. The reaction mixture was then evaporated and the residue was taken up in dichloromethane. This solution was then washed with saturated aqueous NaHCO$_3$ (×4), dried (Na$_2$SO$_4$) and evaporated to give a solid. Crystallization of this material from ethyl acetate-hexane (−20° C.) afforded 4.161 g of the title compound as greenish-gold needles, mp 179°–180° C. Chromatography of the mother liquor (SiO$_2$/ethyl acetate-hexane, 1:1) gave an additional 0.417 g of the pure product. Total yield=4.578 g (97%): IR (KBr) 3318, 1604, 1585 cm$^-$; $^1$H NMR (DMSO-d$_6$, 200 MHz) δ 11.72 (br s, 1H), 7.81 (d, J=9.0 Hz, 1H), 7.56 (t, J=2.8 Hz, 1H), 7.39 (d, J=8.9 Hz, 1H), 6.79 (m, 1H), 2.75 (s, 3H). Anal. Calcd for C$_9$H$_8$N$_2$O$_2$: C, 61.35; H, 4.58; N, 15.90. Found: C, 61.32; H, 4.40; N, 15.96.

5-(4-Methyl-5-nitroindol-3-ylmethyl)-2,2-dimethyl-1,3-dioxane-4,6-dione

An adaption of the procedure of Flaugh was used. Thus, a solution of 4-methyl-5-nitroindole (0.880 g, 5.00 mmol), Meldrum's acid (0.864 g, 6.00 mmol), 37% aqueous formaldehyde (0.5 mL, 6.0 mmol) and D,L-proline (0.029 g, 0.25 mmol) in 25 mL of acetonitrile was stirred at room temperature for 72 h. The resulting yellow slurry was stored at −20° C. and then the cold mixture was filtered. The filtercake was washed with cold acetonitrile and ether, and then it was dried in vacuo to give the title compound (1.055 g, 64%) as a canary-yellow solid, mp 196°–198° C. (dec): IR (KBr) 3338, 1782, 1742 cm$^{-1}$; $^1$H NMR (DMSO-d$_6$, 200 MHz) δ 11.46 (br s, 1H), 7.61 (d, J=8.9 Hz, 1H), 7.32 (d, J=8.9 Hz, 1H), 7.25 (d, J=2.4 Hz, 1H), 4.74 (t, J=5.0 Hz, 1H), 3.64 (d, J=4.9 Hz, 1H), 2.80 (s, 3H), 1.84 (s, 3H), 1.69 (s, 3H). Anal. Calcd for C$_{16}$H$_{16}$N$_2$O$_6$: C, 57.83; H, 4.85; N, 8.43. Found: C, 57.42; H, 4.68; N, 8.52.

F. Ethyl 4-methyl-5-nitro-3-indolepropionate

To a solution of 5-(4-methy-5-nitroindol-3-ylmethyl)-2,2-dimethyl-1,3-dioxane-4,6-dione (1.009 g, 3.04 mmol) in a mixture of pyridine (18 mL) and absolute ethanol (2 mL) was added 0.05 g of copper powder and the mixture was heated to reflux under Ar for 2 h. The cooled mixture was filtered and the filtrate was evaporated in vacuo to give a viscous brown oil. This material was taken up in ethyl acetate and the solution was washed (1N HCl, saturated aqueous $NH_4Cl$, brine), dried ($Na_2SO_4$) and evaporated to give a yellow solid. Trituration with ether gave 423 mg of the title compound as a tan solid. An additional 166 mg of the product could be recovered by evaporation of the supernatant and retrituration with ether. Total yield=671 mg (80%). An analytical sample was crystallized from ethyl acetate-hexane to give tan crystals, mp 105°–106° C.: IR (KBr) 3340, 1717, 1517, 1335 $cm^{-1}$; $^1H$ NMR (DMSO-$d_6$, 200 MHz) δ 11.47 (br s, 1H), 7.63 (d, J=9.0 Hz, 1H), 7.30 (d, J=8.6 Hz, 1H), 7.28 (s, 1H), 4.06 (q, J=7.1 Hz, 2H), 3.18 (t, J=7.1 Hz, 2H), 2.77 (s, 3H), 2.68 (m, 2H), 1.16 (t, J=7.1 Hz, 3H). Anal. Calcd for $C_{14}H_{16}N_2O_4$: C, 60.86; H, 5.84; N, 10.14. Found: C, 60.76; H, 5.74; N, 10.00.

G. 4-Methyl-5-nitro-3-(3-hydroxypropyl)indole

To a suspension of 95% $LiAlH_4$ (0.378 g, 9.44 mmol) in 10 mL of dry THF was added a solution of ethyl 4-methyl-5-nitro-3-indolepropionate (0.650 g, 2.36 mmol) in 2 mL of dry THF, at 0° C. under Ar. After 5 min the cooling bath was removed and stirring was continued at room temperature for 30 min. The reaction was then quenched by the sequential addition of 0.4 mL of water, 0.4 mL of 15% aqueous NaOH and finally 1.2 mL of water. The resulting suspension was diluted with ethyl acetate and then it was filtered and the filtercake was washed with additional ethyl acetate. The filtrate was evaporated and the residue was chromatographed ($SiO_2$/dichloromethane-ethyl acetate, 2:1) to give the title compound (0.458 g, 83%) as a solid. An analytical sample was crystallized from ethyl acetate-hexane to give yellow-orange needles, mp 129°–130° C.: IR (KBr) 3543, 3210, 1616, 1520, 1330 $cm^-$; $^1H$ NMR (DMSO-$d_6$, 200 MHz) δ 11.43 (br s, 1H), 7.63 (d, J=8.9 Hz, 1H), 7.30 (d, J=8.7 Hz, 1H), 7.29 (s, 1H), 4.51 (t, J=5.2 Hz, 1H), 5.20 (dt, J=6.2, 5.4 Hz, 2H), 2.91 (t, J=7.7 Hz, 2H), 2.78 (s, 3H), 1.78 (m, 2H). Anal. Calcd for $C_{12}H_{14}N_2O_3$: C, 61.52; H, 6.02; N, 11.96. Found: C, 61.23; H, 5.85; N, 11.90.

H. 4-Methyl-5-amino-3-(3-hydroxypropyl)indole

To a solution of 4-methyl-5-nitro-3-(3-hydroxypropyl)indole (0.365 g, 1.56 mmol) in 20 mL of absolute ethanol was added 10% palladium-on-charcoal (0.150 g) and the mixture was hydrogenated on a Parr shaker at 50 psi for 0.5 h. The mixture was then filtered through a plug of Celite, the catalyst was washed with additional ethanol and the filtrate was evaporated to give the title compound (0.280 g, 88%) as a solid. An analytical sample was crystallized from ethyl acetate to give cream-coloured needles, mp 141°–142° C.: IR (KBr) 3388, 3180, 1618 $cm^{-1}$; $^1H$ NMR (DMSO-$d_6$, 200 MHz) δ 10.20 (br s, 1H), 6.87 (d, J=8.8 Hz, 1H), 6.83 (s, 1H), 6.50 (d, J=8.3 Hz, 1H), 4.43 (t, J=5.2 Hz, 1H), 4.12 (s, 2H), 3.47 (dt, J=6.4, 5.3 Hz, 2H), 2.79 (t, J=7.7 Hz, 2H), 2.31 (s, 3H), 1.73 (m, 2H). Anal. Calcd for $C_{12}H_{16}N_2O$: C, 70.55; H, 7.90; N, 13.72. Found: C, 70.41; H, 7.89; N, 13.55.

I. 4-Methyl-5-(1,2-dioxo-4-methyl-3-cyclobuten-3-yl)amino-3-(3-hydroxypropyl)indole Method A: To a solution of 4-methyl-5-amino-3-(3-hydroxypropyl)indole (0.260 g, 1.27 mmol) in 9 mL of absolute ethanol was added a solution of 3-(1-methylethoxy))-4-methylcyclobut-3-ene-1,2-dione[2] (0.234 g, 1.52 mmol) in 1 mL of ethanol and the mixture was stirred at room temperature for 18 h. After standing at −20° C. for 3 h, the mixture was filtered. The residue was washed with cold ethanol and then ether, and finally it was dried in vacuo to give 0.126 g of the title compound as an off-white solid, m.p. 179°–181° C. Evaporation of the filtrate and treatment of the residual brown gum with acetonitrile gave an additional 0.166 g of the product as a beige solid. Total yield=0.292 g (77%): IR (KBr) 3425, 3360 (br), 1786, 1718, 1590 (br) $cm^{-1}$; $^1H$ NMR (DMSO-$d_6$, 200 MHz) δ 10.92 (br s, 0.75H), 10.86 (br s, 0.25H), 10.57 (br s, 0.75H), 10.30 (br s, 0.25H), 7.19 (d, J=8.5 Hz, 1H), 7.12 (m, 1H), 6.92 (d, J=8.5 Hz, 0.75H), 6.86 (d, J=8.5 Hz, 0.25H), 4.47 (t, J=5.2 Hz, 1H), (dt, J=6.3, 5.4 Hz, 2H), 2.87 (m, 2H), 2.50 (s, 3H), 2.24 (s, 0.75H), 1.76 (m, 2H), 1.56 (s, 2.25H). Anal. Calcd for $C_{17}H_{18}N_2O_3$. 0.3 $H_2O$: C, 67.22; H, 6.17; N, 9.23. Found: C, 67.26; H, 5.88; N, 9.18.

[2] L. S. Liebeskind, R. W. Fengl, D. R. Wirtz, T. T. Shaw, *J. Org. Chem.* 1988, 53, 2482.

Method B: To a solution of 4-methyl-5-amino-3-(3-hydroxypropyl)indole (0.271 g, 1.33 mmol) in 6 mL of DMF was added triethylamine (0.223 mL, 1.60 mmol), followed by a solution of 3-chloro-4-methylcyclobut-3-ene-1,2-dione[3] (0.208 g, 1.60 mmol) in 1 mL of DMF. The resulting brown solution was stirred at room temperature under Ar for 1 h and then it was concentrated in vacuo to give a viscous oil. The oil was diluted with water and extracted with ethyl acetate (×5). The organic extract was washed (brine, ×4), dried ($Na_2SO_4$) and evaporated to give a dark brown oil. This material was taken up in ethyl acetate and then filtered through a short silica gel column (elution with ethyl acetate) to give the impure product as a light yellow gum. Crystallization from acetonitrile-dichloromethane at −20° C. afforded the title compound (0.272g, 69%) as a cream-coloured solid.

J. 4-Methyl-5-(1,2-dioxo-4-methyl-3-cyclobuten-3-yl)amino-3-(3-methanesulfonyloxy-propyl)-indole To an ice-cold suspension of 4-methyl-5-(1,2-dioxo-4-methyl-3-cyclobuten-3-yl)amino-3-(3-hydroxypropyl)indole (0.235 g, 0.79 mmol) in 5 mL of acetonitrile-THF (4:1) was added triethylamine (0.132 mL, 0.95 mmol), followed by methanesulfonyl chloride (0.074 mL, 0.95 mmol). The mixture was stirred at 0° C. for 2 h and then the cooling bath was removed and stirring continued at room temperature for 17 h. Another 0.026 mL (0.19 mmol) of triethylamine and 0.015 mL (0.19 mmol) of methanesulfonyl chloride were then added and stirring was continued for 30 min. The resulting mixture was diluted with ethyl acetate, washed ($H_2O×2$; brine), dried ($Na_2SO_4$) and evaporated to give a gum. This material was chromatographed ($SiO_2$/ethyl acetate-dichloromethane, 1:1) to give to give the title compound (0.270 g, 91%) as an off-white foam. An analytical sample was obtained by crystallization from ether to give an off-white solid, mp 130°–131° C. (dec): IR (KBr) 3240 (br), 1792, 1727, 1590, 1330, 920 $cm^{-1}$; $^1H$ NMR (DMSO-$d_6$, 200 MHz) δ 11.01 (br s, 0.75H), 10.95 (br s, 0.25H), 10.58 (s, 0.75H), 10.31 (s, 0.25H), 7.23–7.13 (m, 2H), 6.94 (d, J=8.5 Hz, 0.75H), 6.88 (d, J=8.6 Hz, 0.25H), 4.29 (t, J=6.3 Hz, 2H), 3.19 (s, 3H), 2.96 (m, 2H), 2.50 (s, 3H), 2.24 (s, 0.75H), 2.02 (m, 2H), 1.56 (s, 2.25H). Anal. Calcd for $C_{18}H_{20}N_2O_5S$: C, 57.43; H, 5.36; N, 7.44. Found: C, 57.16; H, 5.00; N, 7.34.

[3] D. Bellus, P. Martin, H. Sauter, T. Winkler, *Helv. Chim. Acta* 1980, 63, 1130.

K. 3-[3-[4-(5-Methoxy-4-pyrimidyl)-1-piperazinyl]propyl]4-methyl-5-(1,2-dioxo-4-methyl-3-cyclobuten-3-yl)aminoindole A mixture of 4-methyl-5-(1,2-dioxo-4-methyl-3-cyclobuten-3-yl)amino-3-(3-methanesulfonyloxypropyl)indole (0.154 g, 0.41 mmol), 1-(5-methoxy-4-pyrimidyl)piperazine (0.087 g, 0.45 mmol), finely pulverized KI (0.075 g, 0.45 mmol) and diisopropylethylamine (0.365 mL, 2.1 mmol) in 5 mL of acetonitrile was heated to reflux under Ar for 13 h. The resulting slurry was diluted with ethyl acetate, washed ($H_2O×2$; brine), dried ($Na_2SO_4$) and evaporated to give a light brown gum. Flash chromatography of this gum (SiO₂/MeCN—MeOH—NH₄OH, 90:9:1) afforded the title compound (0.151 g, 78%) as a pale yellow foam. A 142 mg sample of this material was taken up in methanol (ca. 3 mL) and 1N HCl (ca. 3 mL) was added. The resulting solution was concentrated and then stored at −20° C. to give a solid. This material was filtered, washed (1N HCl, acetone, ether) and then dried in vacuo to give the hydrochloride (0.140 g, 77%) as an off-white solid, mp >240° C. (dec): IR (KBr) 3400, 3200, 1784, 1722, 1595 cm⁻¹; ¹H NMR (DMSO-d₆, 200 MHz) δ11.46 (br s, 1H), 11.09 (s, 0.7H), 11.01 (s, 0.3H), 10.62 (s, 0.7H), 10.46 (s, 0.3H), 8.62 (s, 1H), 8.21 (s, 1H), 7.24 (s, 1H), 7.22 (d, J=8.5 Hz, 0.7H), 7.16 (d, J=8.4 Hz, 0.3H), 6.95 (d, J=8.5 Hz, 0.7H), 6.88 (d, J=8.6 Hz, 0.3H), 4.88 (m, 2H), 3.91 (s, 3H), 3.66 (m, 4H), 3.17 (br s, 4H), 2.94 (m, 2H), 2.5–2.6 (m, 2H), 2.52 (s, 3H), 2.26 (s, 0.9H), 2.10 (m, 2H), 1.57 (s, 2.1H). Anal. Calcd for $C_{26}H_{30}N_6O_3 \cdot 2$ HCl $\cdot 1.7$ H₂O $\cdot 0.2$ C₂H₃N $\cdot 0.25$ C₄H₁₀O: C, 54.41; H, 6.42; N, 14.36. Found: C, 54.47; H, 6.80; N, 14.32.

Example 41

4-Ethylthio-3-[3-[4-(5-methoxy-4-pyrimidinyl)-1-piperazinyl]propyl]-5-(1,2-dioxo-4-methyl-3-cyclobuten-3-yl)aminoindole A. 3-(5-Amino-4-ethylthio-3-indolyl)-1-propanol A cold (10°–12° C.) mixture of 3-(5-nitro-3-indolyl)-1-propanol (Example 3: 2.2 g, 10.0 mmol), ethanethiol (7.4 ml, 0.1 mol) and Zn dust (2.0 g, 30.6 mmol) in dry DMF (20 ml) kept under argon was treated portionwise with NH₄Cl which was added at 10 min interval for 3 h while temperature of the mixture was kept between 10°–12° C. After the addition was completed, the reaction mixture was stirred for 3 h and then diluted with THF:EtOAc (1:2, 45 ml) mixture followed by slow addition of water (40 ml). The mixture was filtered on a glass fiber filter and the two phases separated. The aqueous phase was extracted with EtOAc: THF (2:1, 3×40 ml) mixture The organic extracts were combined, washed with water (2×50 ml), dried (MgSO₄) and concentrated in vacuo. The crude material was chromatographed on silica gel dry column using first a mixture of CH₂Cl₂: EtOAc (3:17) and then EtOAc both containing Et₃N (0.5%). Appropriate fractions were concentrated in vacuo affording 3-(5-amino-4-ethylthio-3-indolyl)-1-propanol (0.50 g, 20%); ¹H NMR (DMSO-d₆) δ (ppm): 10.48 (s, 1H, indolic NH), 7.08 (d, J=8.5 Hz, 1H, indolic H-7), 6.94 (d, J=2.3 Hz, 1H, indolic H-2), 6.59 (d, J=8.5 Hz, 1H, indolic H-6), 4.88 (bs, 2H, NH₂), 4.37 (t, J=5.1 Hz, 1H, OH), 3.4–3.6 (m, 2H, H-1), 2.9–3.1 (m, 2H, H-3), 2.65 (q, J=7.4 Hz, 2H, SCH₂CH₃), 1.7–1.9 (m, 2H, H-2), 1.09 (t, J=7.4 Hz, 3H, SCH₂CH₃); also isolated was 3-(5-amino-3-indolyl)-1-propanol (1.0 g, 55%); ¹H NMR (DMSO-d₆) δ (ppm): 10.2 (s, 1H, indolic NH), 7.00 (d, J=8.4 Hz, 1H, indolic H-7), 6.88 (dd, J=2.2 Hz, indolic H-2), 6.63 (d, J=2.0 Hz, 1H, indolic H-4), 6.44 (dd, J=8.4 Hz, J=2.0 Hz, 1H, indolic H-6), 4.4–4.6 (m, 3H, NH₂ and OH), 3.3–3.5 (m, 2H, H-1), 2.5–2.7 (m, 2H, H-3), 1.6–1.9 (m, 2H, H-2).

B. 3-(4-Ethylthio-5-(4-methyl-1,2-dioxocyclobut-3-en-3-yl)amino-3-indolyl)1-propanol A mixture of 3-(5-amino-4-ethylthio-3-indolyl)-1-propanol (0.93 g, 3.7 mmol), 3-chloro-4-methyl-1,2-dioxocyclobut-3-ene (0.58 g, 4.4 mmol) and Et₃N (0.62 ml, 4.4 mmol) in DMF (50 ml) was stirred at 23° C. for 50 h before adding water (200 ml). The aqueous solution was extracted with EtOAc (3×75 ml). The organic extracts were washed with water (50 ml), dried (MgSO₄) and concentrated in vacuo. The crude material was purified on silica gel dry column using first a mixture of CH₂Cl₂:EtOAc (1:4) and then EtOAc:Et₃N (49:1). Appropriate fractions were concentrated in vacuo leaving yellow crystals, 0.815 g, m.p. 119° C., 64%. ¹H NMR (DMSO-d₆) δ (ppm): 11.17, 11.11, 10.80 and 10.51 (4 br s, 2H indolic NH, and 5-NH), 7.4 (br s, 1H), 7.26 (s, 1H), 7.07 (d, J=8.2 Hz, 1H), 4.40 (t, J=5.2 Hz, 1H, OH), 3.46 (t, J=3.5 Hz, 2H after D₂O exchange), 2.95–3.10 (m, 2H, CH₂CH₂CH₂O), 2.66 (br s, 2H, CH₃CH₂S), 2.26 (br s, 1H, CH₃ on dioxocyclobutene), 1.7–1.9 (m, 2H, CH₂CH₂CH₂O), 1.59 (br s, 2H, CH₃ on dioxocyclobutene), 0.9–1.1 (m, 3H, CH₃CH₂S). IR (KBr) n:3420, 3300–3000, 1775, 1728, 1620, 1580 and 1400 cm⁻¹. Anal. calcd. for: $C_{18}H_{20}N_2O_3S$: C 62.77; H 5.85; N 8.13; S 9.31. Found: C 62.75; H 5.85; N 8.20; S 9.25.

C. 4-Ethylthio-3-(3-methanesulfonyloxy-1-propyl)-5-(4-methyl-1,2-dioxocyclobut-3-en-3-yl)amino indole A cold (5° C.) mixture of 3-(4-ethylthio-5-(4-methyl-1,2-dioxocyclobut-3-en-3-yl) amino-3-indolyl)1-propanol (0.708 g, 2.1 mmol) and Et₃N (0.697 ml, 5.0 mmol) in THF:CH₂Cl₂ (1:2, 45 ml) mixture kept under argon atm. was treated dropwise with MsCl (0.387 ml, 5.0 mmol) and stirred at 23° C. for 1.5 h. The reaction mixture was diluted with CH₂Cl₂ (40ml) and washed with H₂O (10ml) and saturated NaHCO₃ solution. The organic phase was dried (MgSO₄) and concentrated in vacuo. The crude material was purified on silica gel dry column using a mixture of CH₂Cl₂:EtOAc (7:3) as eluting solvent. Appropriate fractions were concentrated in vacuo giving a yellow oil, 0.70 g, 79%. ¹H NMR (DMSO-d₆) δ (ppm): 11.26, 11.20, 10.81 and 10.53 (4 br s, 2H, indolic NH and 5-NH), 7.42 (br s, 1H), 7.32 (s, 1H), 7.09 (d, J=8.2 Hz, 1H), 4.27 (t, J=6.4 Hz, 2H, CH₂OSO₂), 3.17 (s, 3H, CH₃SO₂), 3.11 (t, J=7 Hz, 2H, CH₂CH₂CH₂O), 2.67 (br s, 2H, CH₃CH₂S), 2.28 (br, s, 1H, CH₃ of dioxocyclobutene), 2.0–2.15 (m, 2H, CH₂CH₂CH₂O), 1.59 (br s, 2H CH₃ of dioxocyclobutene), 0.9–1.1 (m, 3H, CH₃CH₂S). IR (film) n:3710, 3180, 1783, 1728, 1590, 1340 and 1170 cm⁻¹.

D. 4-Ethylthio-(3-(3-methoxy-4-pyrimidinyl)-1-piperazinyl)-1-propyl)-5-((4-methyl-1,2-dioxocyclobut-3-en-3-yl)amino)indole hydrochloride A mixture of 4-ethylthio-3-(3-methanesulfonyloxy-1-propyl)-5-(4-methyl-1,2-dioxo-cyclobut-3-en-3-yl)amino indole (0.40 g, 0.95 mmol), 4-(5-methoxy-4-pyrimidinyl)piperazine (0.21 g, 1.14 mmol), Et₃N (0.27 ml, 1.9 mmol) and KI (0.166 g, 0.99 mmol) in CH₃CN (18 ml) kept under argon atm. was refluxed for 12 h. The reaction mixture was cooled at 23° C. and diluted with EtOAc (70 ml). The organic solution was washed with K₂CO₃ (1N, 2 ml) and brine, dried (MgSO₄) and concentrated in vacuo. The crude material was purified on dry silica gel column using a mixture of MeOH:EtOAc (1:9) as eluting solvent. Appropriate fractions were concentrated in vacuo leaving a syrup, 0.335 g, 68%. ¹H NMR (DMSO-d₆) δ (ppm): 11.19, 10.8 and 10.5 (3 br s, 2H, indolic NH, 5-NH), 8.23 (s, 1H, pyrimidinyl H), 8.03 (s, 1H, pyrimidinyl H), 7.3–7.5 (m, 1H), 7.39 (br s, 1H), 7.07 (d, J=8.4 Hz, 1H), 3.82 (s, 3H, CH₃O), 3.5–3.7 (m, 3H), 2.9–3.15 (m, 2H), 2.6–2.8 (m, 2H), 2.2–2.3 (m, 1.5H), 1.7–1.95 (m, 2H), 1.59 (br s, 1.5H), 1.0 (t, J=7 Hz, 3H, CH₃CH₂S). An ethanolic solution of the free base was treated with a solution of HCl (1.02N) in EtOH; the solution was diluted with some isopropanol and the yellow crystals (m.p. 188° C. dec.) were filtered. ¹H NMR (DMSO-d₆) δ (ppm): 11.33, 11.27, 10.83 and 10.59 (4 br s, 2H, indolic NH and 5-NH), 8.46 (s, 1H, pyrimidinyl H), 8.18 (s, 1H, pyrimidinyl H), 7.43 (br s, 1H), 7.38 (s, 1H), 7.11 (d, J=7.9 Hz, 1H), 4.7 (d, J=13.9 Hz, 2H), 3.89 (s, 3H, CH₃O), 3.58 (d, J=11.9 Hz, 2H), 3.36 (br t, J=12 Hz, 2H), 3.0–3.3

(m, 6H), 2.67 (br s, 2H, CH$_3$C$\underline{H}_2$S), 2.25 (br s, 1.2 H, CH$_3$ on dioxocyclobutene), 2.0–2.15 (m, 2H, CH$_2$C$\underline{H}_2$CH$_2$N), 1.59 (br s, 1.8 H, CH$_3$ on dioxocyclobutene), 0.99 (br s, 3H, C$\underline{H}_3$CH$_2$S). IR (KBr) n:3700–2200, 1780, 1725, 1628 and 1590 cm$^{-1}$. Anal. calcd. for: C$_{27}$H$_{32}$N$_6$O$_3$S 3.5 HCl 0.5 C$_3$H$_8$O: C 51.29; H 5.92; N 12.59; S 4.80. Found: C 50.93; H 5.76; N 12.64; S 4.90.

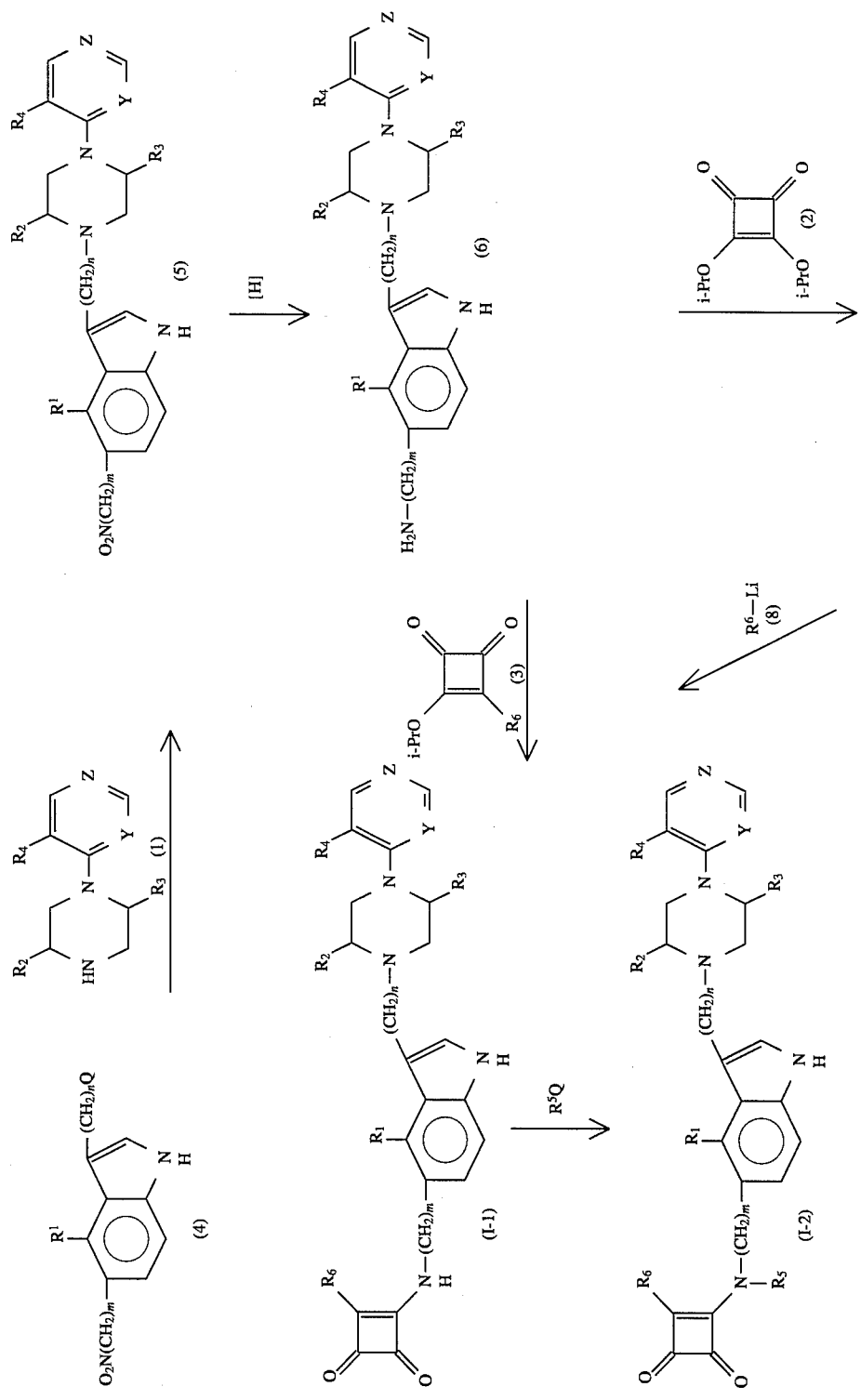

-continued
SCHEME A
Synthesis of Indolyl-Amino-Squarates
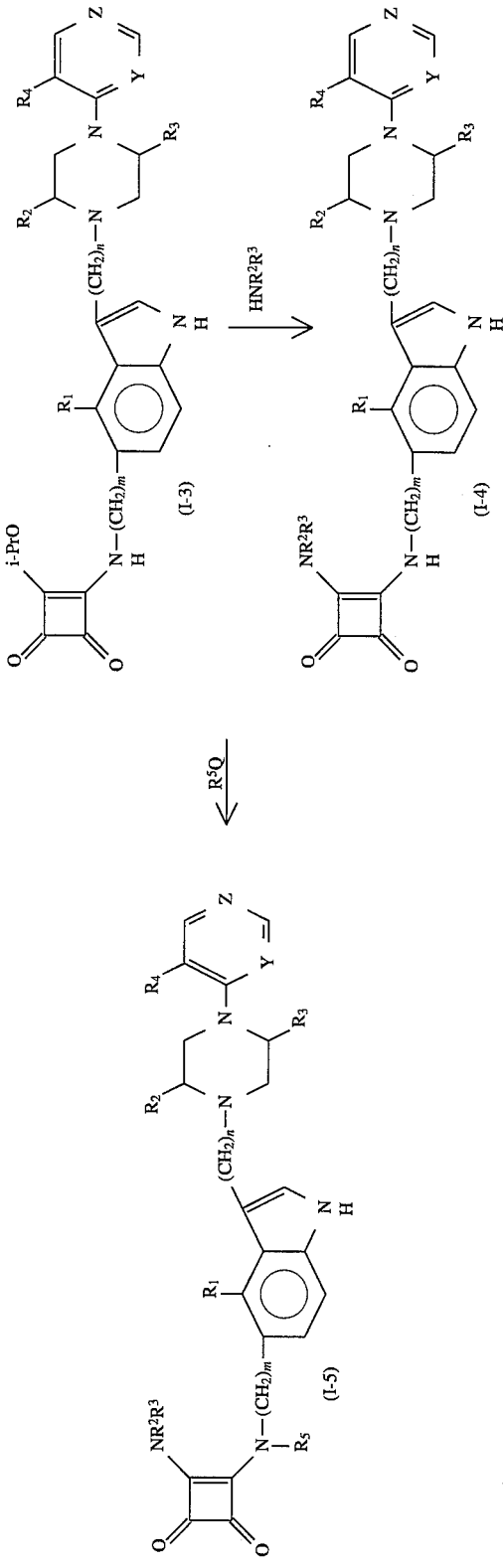

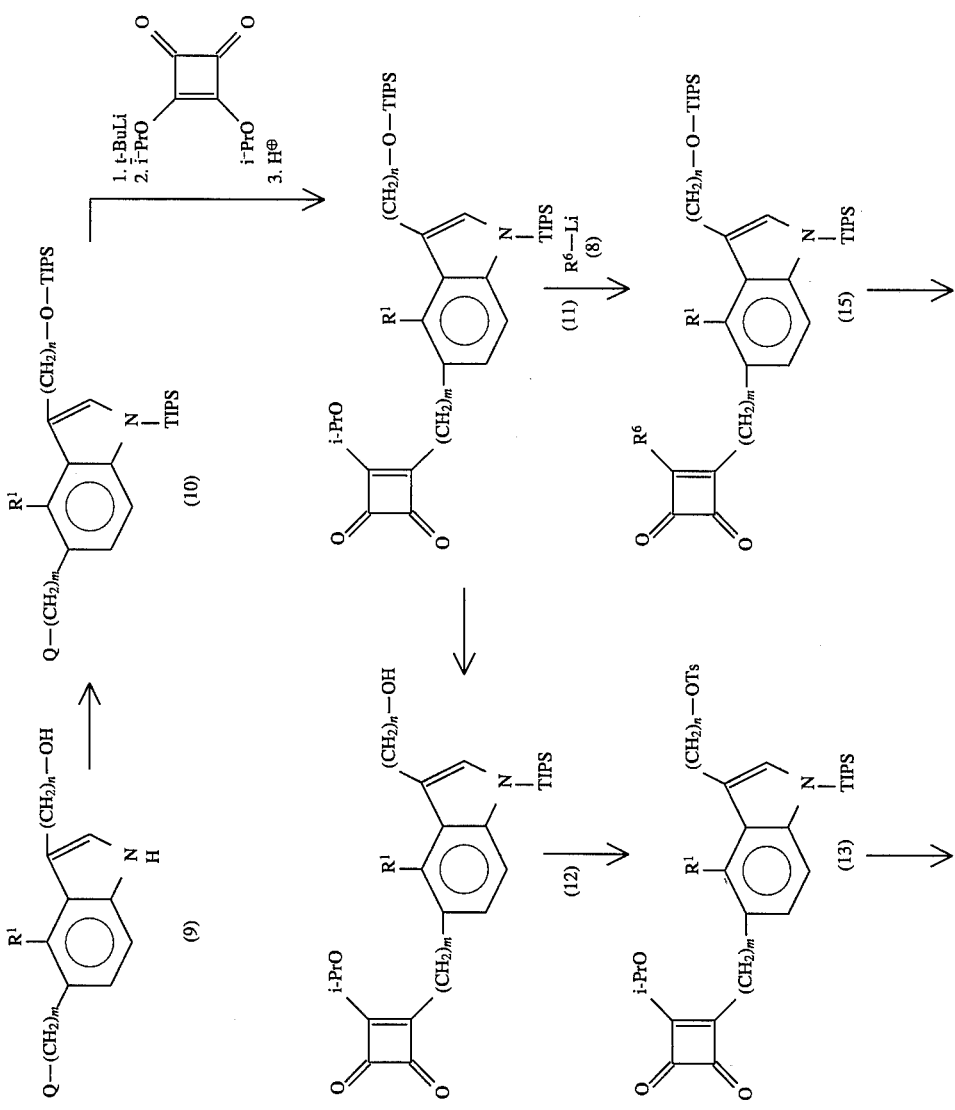

-continued
SCHEME B
SYNTHESIS OF INDOLYL-SQUARATES
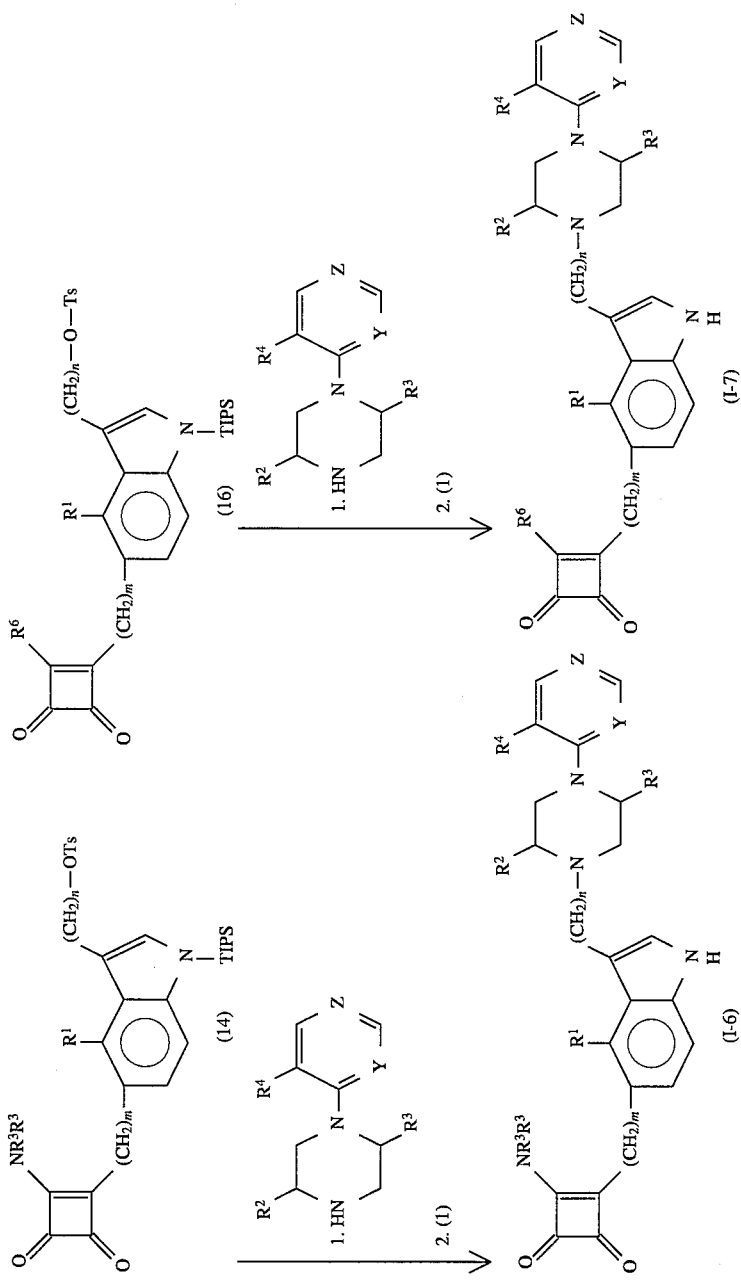

SCHEME C

Synthesis of Intermediates

The following synthetic reactions are intended to provided examples of some of the available methods of preparing chemical intermediates for use in the processes of Schemes A and B.

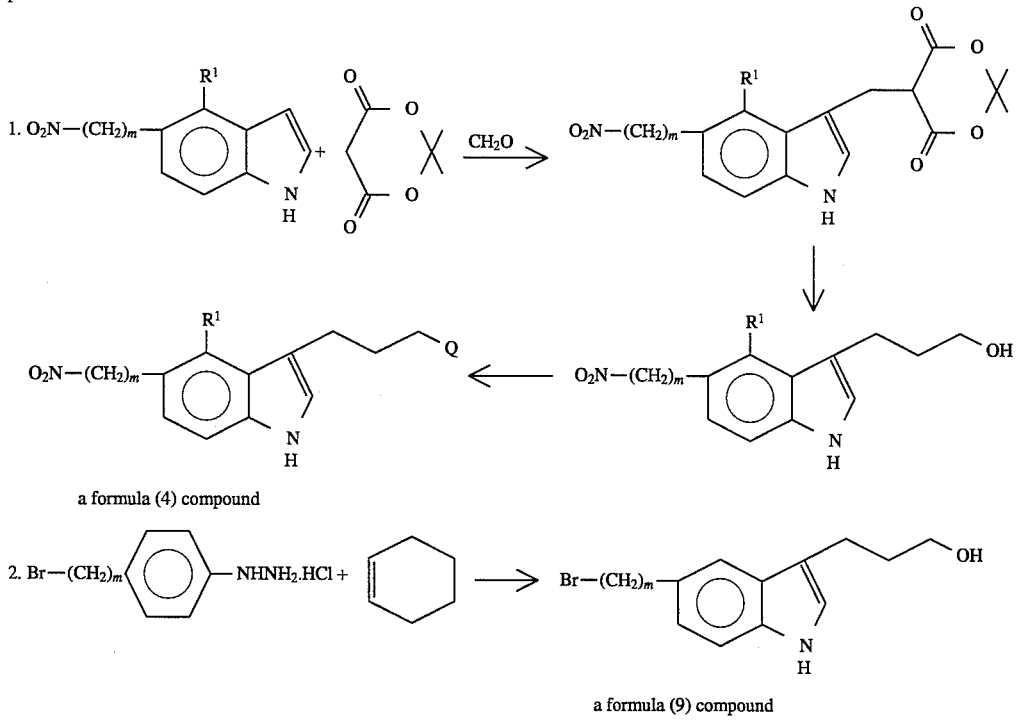

a formula (4) compound

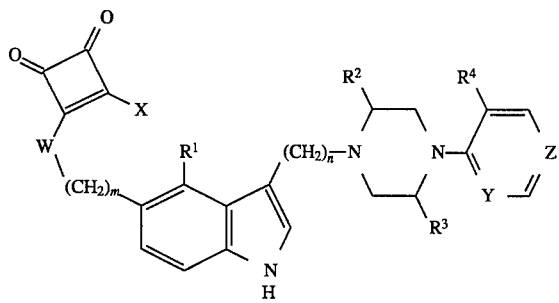

a formula (9) compound

See: *Chem. Abstr.*, 1973, 79

We claim:

1. A compound of Formula I or a pharmaceutically acceptable acid addition salt and/or solvate thereof

I wherein

R$^1$ is selected from hydrogen, halogen, lower alkyl, lower alkoxy and lower alkylthio;

R$^2$ and R$^3$ are independently selected from hydrogen and lower alkyl;

R$^4$ is selected from hydrogen and lower alkoxy;

W is either a single covalent bond or —NR$^5$—, wherein R$^5$ is selected from hydrogen, lower alkyl, lower acyl, and lower alkylsulfonyl;

X is selected from —NR$^2$R$^3$, —OR$^2$, and R$^6$, wherein R$^6$ can be hydrogen, lower alkyl, C$_{5-7}$ cycloalkyl, phenyl, and phenyl-lower alkyl;

Y and Z are independently selected from N and CH with the proviso that both Y and Z cannot be CH simultaneously;

m is selected from zero and the integers 1 to 3; and n is selected from the integers 1 to 5.

2. A compound of claim 1 wherein W is a single covalent carbon-carbon bond.

3. A compound of claim 1 wherein W is —NR$^5$—.

4. A compound of claim 1 wherein m is zero and n is 3.

5. A compound of claim 2 selected from the group consisting of 3-[3-[4-(5-methoxy-4-pyrimidinyl)-1-piperazinyl)propyl]-5-(1,2-dioxo-4-methylamino-3-cyclobuten-3-yl)indole; 3-[3-[4-(5-methoxy-4-pyrimidinyl)-1-piperazinyl]propyl]-5-(1,2-dioxo-4-amino-3-cyclobuten-3-yl)indole; 3-[3-[4-(5-methoxy-4-pyrimidinyl)-1-piperazinyl]propyl]-5-(1,2-dioxo-4-isopropylamino-3-cyclobuten-3-yl)indole; 3-[3-[4-(5-methoxy-4-pyrimidyl)-1-piperazinyl]propyl]-5-(1,2-dioxo-4-t-butylamino-3-cyclobuten-3-yl)indole.

6. A compound of claim 3 selected from the group consisting of 3-[3-[4-(5-methoxy-4-pyrimidinyl)-1-piperazinyl]propyl]-5-[(1,2-dioxo-4-methyl-3-cyclobuten-3-yl)aminomethyl]indole; 3-[3-[4-(5-methoxy-4-pyrimidyl)-1-piperazinyl]propyl]-5-(1,2-dioxo-4-methyl-3-cyclobuten-3-yl)amino-1H-indole; 3-[[3-[3-[4-(3-methoxy-4-pyridinyl)-1-piperazinyl]propyl]-1H-indol-5-yl]amino]-4-methyl-3-cyclobutene-1,2-dione; 3-[[3-[3-(2-pyridinyl)-1-piperazinyl]propyl]-1H-indol-5-yl]amino]-4-methyl-3-cyclobutene-1,2-dione; 3-[[3-[3-[3-2-pyridinyl)-1-piperazinyl]propyl]-1H-indol-5-yl]amino]-4-methyl-3-cyclobutene-1,2-dione; 3-[3-[4-(5-methoxy-4-pyrimidyl)-1- piperazinyl]propyl]-5-(1,2-dioxo-3-cyclobuten-3-yl)amino-1H-indole; 3-[3-[4-(5-methoxy-4-pyrimidyl)-3-methyl-1-piperazinyl]propyl]-5-(1,2-dioxo-3-cyclobuten-3-yl)amino-1H-indole; 3-[3-[4-(5-methoxy-4-pyrimidyl)-2-methyl-1-piperazinyl]propyl]-5-(1,2-dioxo-3-cyclobuten-3-yl)amino-1H-indole; 3-[3-[4-(5-methoxy-4-pyrimidyl)-3-methyl-1-piperazinyl]propyl]-5-(1,2-dioxo-4-methyl-3-cyclobuten-3-yl)amino-1H-indole; 3-[3-[4-(5-methoxy-4-pyrimidyl)-2-methyl-1piperazinyl]propyl]-5-(1,2-dioxo-4-methyl-3-cyclobuten-3-yl)amino-1H-indole; 3-[3-[4-(5-methoxy-4-pyrimidyl)-1-piperazinyl]propyl]-5-(1,2-dioxo-4-butyl-3-cyclobuten-3-yl)amino-1H-indole; 3-[3-[4-(5-methoxy-4-pyrimidyl)-1-piperazinyl]propyl]-5-(1,2-dioxo-3-cyclobuten-3-yl)methylamino-1H-indole; 3-[3-[4-(5-methoxy-4-pyrimidyl)-1-piperazinyl]propyl]-5-[1,2-dioxo-4-(1-methylethoxy)-3-cyclobuten-3-yl]amino-1H-indole; 3-[3-[4-(5-methoxy-4-pyrimidyl)-1-piperazinyl]propyl]-5-(1,2-dioxo-4-hydroxy-3-cyclobuten-3-yl)amino-1H-indole; 3-[3-[4-(5-methoxy-4-pyrimidyl)-1-piperazinyl]propyl]-5-(1,2-dioxo-4-methylamino-3-cyclobuten-3-yl)amino-1H-indole; 3-[3-[4-(5-methoxy-4-pyrimidyl)-1-piperazinyl]propyl]-5-(1,2-dioxo-4-amino-3-cyclobuten-3-yl)amino-1H-indole; 3-[3-[4-(5-methoxy-4-pyrimidyl)-1-piperazinyl]propyl]-5-(1,2-dioxo-4-dimethylamino-3-cyclobuten-3-yl)amino-1H-indole; 3-[3-[4-(5-methoxy-4-pyrimidinyl)-1-piperazinyl]propyl]-5-(1,2-dioxo-4-methyl-3-cyclobuten-3-yl)amino-1H-indole; 4-ethylthio-3-[3-[4-(5-methoxy-4-pyrimidinyl)-1-piperazinyl]propyl]-5-(1,2-dioxo-4-methyl-3-cyclobuten-3-yl)amino-1H-indole.

7. The compound of claim 6, 3-[3-[4-(5-methoxy-4-pyrimidyl)-1-piperazinyl]propyl]-5-(1,2-dioxo-4-methyl-3-cyclobuten-3-yl)amino-1H-indole.

8. A method for treating vascular headaches, consisting of migraine and cluster headaches, by administering a therapeutically effective amount of a compound claimed in claim 1 to a person suffering from a vascular headache.

9. A method for preventing vascular headaches, consisting of migraine and cluster headaches, by administering a prophylactically effective amount of a compound claimed in claim 1 to a person suffering the onset of a vascular headache.

10. A pharmaceutical composition in unit dosage form suitable for systemic administration to a person at risk of or suffering a vascular headache, the composition comprising a pharmaceutical carrier and from about 1 to 500 mg of a compound claimed in claim 1.

\* \* \* \* \*